(12) United States Patent
Marshall et al.

(10) Patent No.: US 9,964,495 B1
(45) Date of Patent: May 8, 2018

(54) METHOD AND SYSTEM FOR SPATIALLY-RESOLVED 3-DIMENSIONAL CHARACTERIZATION OF NEAR-FIELD SPRAYS

(71) Applicant: UNIVERSITY OF MARYLAND, College Park, MD (US)

(72) Inventors: Andre W. Marshall, University Park, MD (US); Ning Ren, Norwood, MA (US)

(73) Assignee: University of Maryland, College Park, MD (US)

( * ) Notice: Subject to any disclaimer, the term of this patent is extended or adjusted under 35 U.S.C. 154(b) by 372 days.

(21) Appl. No.: 14/070,674

(22) Filed: Nov. 4, 2013

Related U.S. Application Data

(60) Provisional application No. 61/721,932, filed on Nov. 2, 2012.

(51) Int. Cl.
*H04N 13/02* (2006.01)
*G01N 21/85* (2006.01)
*B05B 12/08* (2006.01)
*G06T 7/20* (2017.01)

(52) U.S. Cl.
CPC ........... *G01N 21/85* (2013.01); *B05B 12/082* (2013.01); *G06T 7/20* (2013.01)

(58) Field of Classification Search
CPC .............................. G06F 17/00; A62C 31/02
USPC ............................................ 702/162; 348/46
See application file for complete search history.

(56) References Cited

U.S. PATENT DOCUMENTS

2010/0225912 A1* 9/2010 Sivathanu ........... G01M 99/008
356/336

FOREIGN PATENT DOCUMENTS

JP 2003175124 A * 6/2003

OTHER PUBLICATIONS

David Thomas Sheppard (Spray Characteristics of Fire Sprinklers, Prepared for U.S. Department of Commerce Building and Fire Research Laboratory National Institute of Standards and Technology Gaithersburg, MD 20899-8663, Jun. 2002, 206 pages).*
C. Clanet, et al., Life of a Smooth Liquid Sheet, Journal of Fluid Mechanics, vol. 462, pp. 307-340, 2002.
C. Clan et al., Life of a Flapping Liquid Sheet, Journal of Fluid Mechanics, vol. 462, pp. 341-363, 2002.

(Continued)

*Primary Examiner* — Jamie Atala
*Assistant Examiner* — Masum Billah
(74) *Attorney, Agent, or Firm* — Rosenberg, Klein & Lee

(57) ABSTRACT

Near-field spray characteristics are established from local measurements which are acquired by data acquisition subsystem capable of complete scanning of the area (volume) of interest in the spray which uses different laser-based probes (shadowgraphy, PIV, diffraction) to obtain drops related measurements. A mechanical patternator measures volume flux distribution of the spray under study. The measurement data are post-processed to obtain spatially-resolved spray characteristics which are mapped in a spherical coordinate system consistent with the kinematics of the spray. A data compression scheme is used to generate compact analytical functions describing the nozzle spray based on the measurement data. These analytical functions may be useful for initiating the nozzle spray in computational fluid dynamics (CFD) based spray dispersion and fire suppression modeling.

21 Claims, 12 Drawing Sheets

(56) References Cited

OTHER PUBLICATIONS

H. Z. You, Investigation of Spray Patterns of Selected Sprinklers with the FMRC Drop Size Measuring System, First International Symposium on Fire Safety Science, New York, pp. 1165-1176, 1986.

J. Widmann, et al., Non-Intrusive Measurements in Fire Sprinkler Sprays, Fire Technology, vol. 37, pp. 297-315, 2001.

J. Widmann, et al., Phase Doppler Interferometry Measurements in Water Spray Produced by Residential Fire Sprinklers, Fire Safety Journal, vol. 36, pp. 545-567, 2001.

D. T. Sheppard, et al., Understanding Sprinkler Sprays: Trajectory Analysis, NISTIR 6561, National Institute of Standards and Technology, Gaithersburg, MD, 2000.

D. T. Sheppard, Spray Characteristics of Fire Sprinkler, NIST GCR 02-838, National Institute of Standards and Technology, Gaithersburg, MD, 2002.

A. Blum, Discharge Characteristics of Canonical Sprinkler Sprays, M.S. Thesis, University of Maryland-College Park, 2006.

N. Ren, Analysis of the Initial Spray from Canonical Fire Suppression Nozzles, M.S. Thesis, University of Maryland-College Park, 2007.

C. T. Do, Stream-wise Discharge Characteristics of Pendent Sprinkler Sprays, M.S. Thesis, University of Maryland-College Park, 2007.

K. McGrattan, et al., Fire Dynamics Simulator (Version 5), Technical Reference Guide, NIST Special Publication 1018-5, 2008.

\* cited by examiner

METHOD AND SYSTEM FOR SPATIALLY-RESOLVED 3-DIMENSIONAL CHARACTERIZATION OF NEAR-FIELD SPRAYS

STATEMENT REGARDING FEDERALLY SPONSORED RESEARCH OR DEVELOPMENT

The development of the invention described herein was funded by NSF under Grant No. CBET0645063. The U.S. Government has certain rights in this invention.

REFERENCE TO THE RELATED APPLICATIONS

This Utility Patent Application is based on the Provisional Patent Application No. 61/721,932 filed on 2 Nov. 2012.

FIELD OF THE INVENTION

The present invention relates to characterization of sprays produced by nozzles (sprinklers), and in particular to quantification and precise analytical description of the detailed structure of near-field sprays in a broad spectrum of applications including fire suppression systems, microelectronic manufacturing, etc.

More in particular, the present invention relates to an advanced software-supported complete 3-Dimensional (3-D) spatially-resolved sprays characterization methodology using a minimally intrusive scanning technique capable of complete direct scan of the sprays to produce detailed measurements of the sprays' parameters which are subsequently expressed in terms of compact basis functions providing physically rational unprecedentally accurate representation of the complex sprays.

In addition, the present invention is directed to a software-supported Spatially-resolved Spray Scanning System (SSSS) designed as a minimally intrusive diagnostic tool for highly resolved direct visualization of sprays obtained through complete scan of the sprays to attain precise near-field sprays characterization. The SSSS integrates nozzle rotation sub-system, automatic flux acquisition sub-system, and laser-based drops' parameters measurement sub-system into a spray scanner operated by a control computer which coordinates and synchronizes the scanning operation with the azimuthal displacement of the nozzle under study, records measurement results and locations, assists in converting the measurements results into compactly presented spray characteristics, and facilitates in data interpretation with physically meaningful coefficients capable of generating the stochastic spray for computational analysis.

Further, the present invention relates to precise characterization technique for sprays produced by nozzles which uses (a) laser-based measurements of sprays' characteristics which requires only a limited number of measurements at select assessment (interrogation) stations, (b) data compression approach applied to the measured sprays' characteristics to create a product database and a model/representation of the sprays suited for modeling the sprays in computer simulations, (c) nozzle design software which incorporates the product database, and (d) a game-engine tangible medium for interactive real-time graphics based design and evaluation.

Further, the present invention relates to fire suppression (and other sprays producing) systems design tool which generates compact basis functions based on measured comprehensive characteristics of sprays to create a database which may be incorporated into a fire suppression system design software for a designer's use.

The present invention also relates to a computer system configured to facilitate post-processing of flux' and drops' measurements required to characterize dispersion of a spray produced by a nozzle in terms of basis functions to develop a product database which may be incorporated into a game-engine to develop fire suppression systems design software for interactive real-time graphics based design and performance evaluation.

BACKGROUND OF THE INVENTION

Sprays are used in a variety of technology intensive industries from microelectronic manufacturing to fire-protection applications.

Despite diversity in size, shape, and design details, most nozzles, e.g. modern fire sprinklers 10, shown FIGS. 1A-1B, use the same fundamental method of spray generation. Water is initially forced through an orifice 12 to produce a continuous water jet. This jet then impinges onto a deflector 14 to form a thin sheet 16 of water. The sheet subsequently disintegrates into ring-like ligaments 18 and ultimately into a complex population of drops 20 forming a spray.

Because of the complexity of the physical processes associated with atomizing a continuous stream of fluid into a spray and the difficulty associated with characterizing atomization details, spray formation and its relationship to injection conditions is poorly understood. As a result, spray related development is inhibited by analytical concessions, which rely primarily on 'cut and try' and empirical approaches.

However, as computer based design tools become increasingly popular, detailed atomization models will be needed for computer-aided development, analysis, and evaluation of spray devices and systems. It is essential to precisely characterize engineered sprays in order to develop models to describe their behavior and to leverage this understanding for advancement in spray technology.

The sprinkler atomization process can be divided into stages for focused measurements and analysis. Several fundamental atomization studies have developed theories to describe physical processes relevant to fire sprinkler spray generation. There is also a separate body of more applied research focused on quantifying discharge characteristics (i.e., drops' size and velocity) and dispersion behavior from fire sprinklers.

Numerous fundamental studies have been conducted to examine the atomization process responsible for transforming continuous liquid streams into discrete drops. These studies considered the fundamental physical processes leading to atomization and their dependence on injection and environmental conditions. N. Dombrowski, et al., ("The Effect of Ambient Density on Drop Formation in Sprays," *Chemical Engineering Science*, Vol. 17, pp. 291-305, 1962) developed mathematical equations to describe sinuous break-up and dilatational break-up modes ultimately leading to a prediction of characteristic drop size.

On the other hand, J. C. P. Huang ("The Break-up of Axisymmetric Liquid Sheets," *Journal of Fluid Mechanics*, Vol. 43, pp. 305-319, 1970) utilized a high-speed motion photographic technique to study the break-up mechanisms of liquid sheets formed by the impingement of two co-axial jets. Huang reported three break-up regimes and their trends by plotting the ratios of break-up radii over nozzle radius against the jet Weber number, We.

More recently, C. Clanet, et al. conducted a series of experiments to study the formation and disintegration of smooth and flapping liquid sheets, generated by impinging a jet onto a flat deflector ("Life of a Smooth Liquid Sheet," *Journal of Fluid Mechanics*, Vol. 462, pp. 307-340, 2002; and "Life of a Flapping Liquid Sheet," *Journal of Fluid Mechanics*, Vol. 462, pp. 341-363, 2002). They found break-up distance trends similar to those reported by Huang despite differences in their experimental configuration.

A number of experiments have been conducted over the past four decades to measure the discharge characteristics of sprinkler sprays. These experiments utilized a wide range of experimental methods and diagnostics, including simple short time exposure photography and more advanced diagnostic techniques such as Phase Doppler Interferometer (PDI) and Particle Image Velocimetry (PIV). P. H. Dundas ("Technical Report Optimization of Sprinkler Fire Protection the Scaling of Sprinkler Discharge: Prediction of Drop Size," Factory Mutual Research Corporation, Norwood, Mass., June 1974) evaluated scaling laws proposed by Heskestad, $d_{V50}=NWe^{-1/3}$ where $d_{V50}$ is the volumetric median diameter, $D_0$ is the nozzle diameter, and N is a constant ranging from 1.74 to 3.21.

More than a decade later, H. Z. Yu ("Investigation of Spray Patterns of Selected Sprinklers with the FMRC Drop Size Measuring System," *First International Symposium on Fire Safety Science*, New York, pp. 1165-1176, 1986) employed a laser-based imaging technique to measure drop size from three upright sprinklers. The measured overall characteristic drop size followed a $We^{-1/3}$ scaling law consistent with Dundas's sprinkler measurements.

The PDI technique was first validated and utilized by J. F. Widmann, et al, ("Non-Intrusive Measurements in Fire Sprinkler Sprays," *Fire Technology*, Vol. 37, pp. 297-315, 2001; and "Phase Doppler Interferometry Measurements in Water Spray Produced by Residential Fire Sprinklers," *Fire Safety Journal*, Vol. 36, pp. 545-567, 2001) to measure the spray from four sprinklers with orifice diameters.

Soon after Widmann, D. T. Sheppard, et al. ("Understanding Sprinkler Sprays: Trajectory Analysis," NISTIR 6561, National Institute of Standards and Technology, Gaithersburg, Md., 2000; and "Spray Characteristic of Fire Sprinkler," NIST GCR 02-838, National Institute of Standards and Technology, Gaithersburg, Md., 2002) made their contribution to the database of sprinkler spray measurements through a comprehensive set of experiments on sixteen commercially available pendant and upright sprinklers. Employing PDI techniques, Sheppard obtained local measurements of drop size at various azimuthal and elevation angles. Sheppard also applied the PIV technique to measure drop velocity. The velocity magnitude data, presented in spherical coordinates with the sprinkler head at the center, showed significant variation with elevation angle.

Most recently, sprinkler measurements were conducted at the University of Maryland by A. Blum, et al., ("Discharge Characteristics of Canonical Sprinkler Sprays," M. S. Thesis, University of Maryland-College Park, 2006.), N. Ren ("Analysis of the Initial Spray from Canonical Fire Suppression Nozzles," M. S. Thesis, University of Maryland-College Park, 2007), and C. T. Do ("Stream-wise Discharge Characteristics of Pendent Sprinkler Sprays," M. S. Thesis, University of Maryland-College Park, 2007). They explored sprinkler geometry effects by using different nozzle configurations. In the simplest configuration (referred to as the Basis Nozzle), a jet was orthogonally injected onto a flat circular deflector disk, while a commercially available Tyco D3 spray nozzle (referred to as the Standard Nozzle) was used to represent a more complex nozzle similar to that of an actual fire sprinkler.

High-speed flash photography and Planar Laser Induced Fluorescence (PLIF) techniques were employed to measure sheet topologies and sheet break-up distances. It was found that two distinct streams are formed from flow deflected along the tines and flow passing through the slots. It was also found that the break-up distances produced by the Basis and Standard Nozzles follow a $We^{-1/3}$ scaling law.

Shadowgraphy was also used to measure local and overall drop size distributions. These distributions also followed scaling laws, $We^{-1/3}$ for the Standard Nozzles and a much weaker We dependence for the basis Nozzles.

Shadowgraphy measurements have revealed new scaling laws for the stream breakup location and drop size, which move beyond conventional parameters such as the orifice diameter and the injection Weber number. These scaling laws include parameters related to the flow split between the tine and the slot, the deflector diameter, and turbulence levels at the injector inlet.

Although these scaling laws reveal important connections between the sprinkler geometry and the overall spray characteristics, they are insufficient for specifying the initial spray characteristics. A technique for accurate characterization of initial sprays is still a long lasting need.

Traditionally, sprinkler performance has been evaluated through testing (as described previously). However, with the advent of the Fire Dynamics Simulator (FDS) first released in 2000 (K. McGrattan, et al., Fire Dynamics Simulator (Version 5), Technical Reference Guide, NIST Special Publication 1018-5, 2008), modeling of fire phenomena with computational fluid dynamics (CFD) tools is becoming increasingly popular. Some early computational studies (R. L. Alpert in "Numerical modeling of the interaction between automatic sprinkler sprays and fire plumes," *Fire Safety Journal*, Vol. 9, pp. 157-163, 1985; and W. K. Chow, et al., in "Numerical simulation on cooling of the fire-induced air flow by sprinkler water sprays," Fire Safety Journal, Vol. 17, pp. 264-290, 1991) focused on studying the interaction between fire plumes and sprinkler sprays. However, without detailed knowledge of initial spray characteristics, dispersion predictions, typically quantified through analysis of volume flux to the floor does not meet the required need.

In order to predict the initial spray, an atomization model needs to accurately predict the flux distribution very close to the injector where the spray is formed. Predicting atomization based on first principles is now within reach using expensive computational methods such as Volume of Fluid (VOF) analysis.

However, the grid requirements to resolve the smallest length scales important for atomization make this exercise all but impractical for engineering applications.

Based on recent measurements and analysis, it is possible to imagine a pathway toward integration of reliable high fidelity sprinkler spray characteristics into CFD simulations for detailed fire suppression analysis. This pathway begins with understanding the topology of the streams generated by the sprinkler deflector which informs the development of physics based atomization models along with the development of measurement approaches to support their development.

Because of the complexity of the spray, these measurements will necessarily consist of enormous quantity of drop realizations, which will require a frame work to extract useful discharge characteristics and a database to facilitate the understanding of sprinkler geometry and injection pressure effects on the discharge characteristics of the spray.

A comprehensive methodology for detailed measurements near the sprinkler discharge (i.e. the near-field) to completely characterize the initial sprinkler spray in effective fashion and with high accuracy, and free shortcomings of the early studies, is a long-lasting need for fire suppression systems.

It is also desirable to integrate highly detailed precise direct measurements of sprays with a comprehensive framework for representing these detailed measurements in a compact format for spray analysis and modeling. This framework would help to provide the opportunity to establish a high-fidelity spray initiation database (at least for the most popular sprinkler models) useful for widespread and consistent sprinkler dispersion and fire suppression analysis.

SUMMARY OF THE INVENTION

It is therefore an object of the present invention to provide a technique supporting detailed measurements conducted in close proximity to the sprinkle discharge (i.e., the near-field spray) to characterize the initial sprinkler spray.

It is another object of the present invention to provide a system and method which would result in a complete 3D (three-dimensional) characterization of sprays, e.g., fire suppression sprays, to provide insight into the spray structure while at the same time providing the ability to predict the dispersion of fire suppression sprays with unprecedented accuracy.

It is also an object of the present invention to provide a system and method based on Spatially-resolved Spray Scanning System (SSSS) which combines: 1) minimally intrusive diagnostics; 2) analytical approaches; and 3) engineering practices to quantify detailed fire suppression spray characteristics while representing these spatially-resolved spray details in a convenient format, with the minimally intrusive diagnostics combined into a unique measurement approach implemented through complete direct scanning of sprays for near-field spray characterization. The analytical approaches have been established to convert the measurements of the scanning system into a physically rational format using basis functions to provide a compact analytical description of the spray while providing a framework for insight into the spray features as well as for spray pattern comparisons of various nozzles. New engineering practices are enabled with the SSSS, whose capability to completely characterize the three dimensional stochastic structure of the initial spray makes it possible to accurately predict the dispersion and wetting performance of nozzles.

It is an additional object of the present invention to provide the Spatially-resolved Spray Scanning System which can empower fire suppression system designers to directly evaluate the wetting performance of their designs (as an alternative to ad hoc analysis without detailed knowledge of nozzle behavior).

It is still another object of the present invention to provide a unique spray scanning data acquisition system for complete spray scanning which would include a laser-based probing sub-system using a number of probes (shadowgraphy, diffraction, Particles Tracking Velocimetry, etc.) displaceable regarding the spray to a number of interrogation (assessment) stations for complete scanning of an area (or volume) of interest in the spray under study. The probing sub-system operation for acquiring drops' sizes, quantities and velocities would be augmented by using also an automatic flux acquisition system. A nozzle rotation sub-system would slowly rotate the nozzle of interest about its axis allowing the flux acquisition system to remain stationary and to minimize the traversing requirements of the laser diagnostics (probing sub-system). The measurement data are synchronized in the system by a computer with the azimuthal position of the nozzle providing a spherical scan of the nozzle flux, as well as spherical scans of the drops' size, velocity, and/or drops' concentration. The computer scans the measurements spheres, synchronizes the measurements and movement, and records measurement locations. The subject system would greatly improve measurement fidelity while reducing the effort required to obtain spatially resolved spray information.

It is an additional object of the present invention to provide a new approach to completely characterize the initial fire suppression spray, to automate the process, to standardize the output in a physically rational format while retaining the fidelity needed for specification of the spray for detailed computational based fire suppression analysis. The ability to quantify and analytically describe the detailed structure of the spray is envisioned as being able to provide insight to sprinkler designers in new nozzles development. Further, these innovations may make it possible to characterize entire product lines of fire suppression nozzles to establish databases to support wetting analysis useful in fire suppression system design.

It is a further object of the present invention to provide a spray characterization technique capable of characterizing large-scale sprays (e.g., used in fire suppression applications), as well as small scale sprays (e.g., in microelectronic applications), and applicable for sprinklers, fire suppression nozzles, irrigation nozzles, specialty nozzles, etc., where capabilities of high spatial resolution and direct measurements are easily combined with software to predict wetting performance of the sprays. This is useful in supporting quality control and nozzle development work, and capable of potential integration with dispersion software that provides unique value for product development and system design.

In one aspect, the present invention constitutes a system for highly spatially-resolved characterization of near-field sprays. The subject system includes a nozzle which produces a spray under study. The nozzle is capable of controllable azimuthal displacement about its central axis.

The system is further is built with a data acquisition sub-system for obtaining measurement data characterizing the spray under study. The data acquisition system uniquely combines:

(a) a laser-based probing sub-system controllably displaceable with regard to the spray under study for performing a complete scanning of an area (volume) of interest in the spray to directly acquire images of the spray and drops' related measurement data, and (b) a patternator sub-system disposed at a predetermined position relative to the nozzle in operative connection with the spray under study to obtain the flux related measurement data.

A controller sub-system is operatively coupled to the nozzle and to the data acquisition sub-system for the controllable azimuthal displacement of the nozzle and translation (in X-Y-Z directions, as needed) of the laser-based probing sub-system to interrogation stations for complete scanning of the area (volume) of interest in the spray in a coordinated fashion with the rotation of the nozzle, as well as the actuation of the laser-based probing sub-system's scanning operation.

A computer sub-system is operatively coupled to the data acquisition sub-system. The computer sub-system is configured to process the measurement data received from the data acquisition sub-system and to calculate spray characterization data based on the measurement data. The computer sub-system is also configured to instruct the controller sub-system as to synchronized operation of all sub-systems and to ensure tracking of the measurement data sampling to the locations of the interrogation-stations, as well as the azimuthal displacement of the nozzle.

Preferably, a data compression unit is operatively coupled to the computer sub-system to receive the spray characterization data. The data compression unit is configured to generate basis functions describing the spray under study in a compact fashion.

A post-processing software unit is operatively coupled to the computer sub-system (or residing in the computer sub-system) to process the measurement data acquired by the data acquisition sub-system.

The data acquisition sub-system is positioned with regard to the nozzle to obtain the measurement data characterizing near-field spray produced by the nozzle under study. The post-processing software unit is configured to process the near-field spray measurement data to generate the near-field spray characteristics. The near-field spray characteristics include drops' size and velocity distribution characteristics obtained from the laser-based probing sub-system's measurements and volume flux distribution characteristics of the near-field spray under study obtained from the patternator sub-system measurements.

The raw measurement data and images are saved in an acquisition memory unit which is operatively coupled to the data acquisition unit. The acquisition memory unit is in the form of the RAM in the acquisition computer. The measurement data also may be transferred to data storage disks, as well as, a solid-state memory. A memory structure also may be used for saving near-field spray characteristics generated by the post-processing software unit, as well as spray parameters, compacted spray characteristics, images, product databases, etc., output from the computer sub-systems.

A mapping unit is employed in the subject system which is operatively coupled to the post-processing software unit and is configured to map the near-field spray characteristics in a spherical coordinate system consistent with the kinematics of the near-field spray under study.

Preferably, a coefficients and parameters calculation unit is operatively coupled to the post-processing software unit and configured to generate average values and profile shapes for the compact functions (when the compact functions include Legendre polynomials and Gaussian functions), and further to calculate coefficients determined from the nozzle's geometry (when the compact functions include Fourier series).

The subject system further comprises a spray modeling unit operatively coupled to the data compression unit. The spray modeling unit is configured to characterize the spray under study in terms of the compact functions, as well as to create a product database for the nozzle of interest.

The computer sub-system is operatively coupled to the controller sub-system to instruct the controller sub-system as to desired coordinates and actuation of the controllable azimuthal displacement of the nozzle and controllable motion of the probing sub-system with regard to at least one of the plurality of interrogation stations of the area (volume) of interest in the spray under study.

The probing sub-systems may include a number of laser-based probing technologies. For example, a shadowgraphy unit may be used for measuring drops' size, quantity, and velocity in a course spray under study. The shadowgraphy unit generates images of drops obtained during the scanning of the area of interest in the spray under study, which are subsequently processed by the computer sub-system to obtain spatial distribution of drops' size, quantity and velocity.

The probing sub-system further may use a laser-based diffraction probing unit for sizing drops in a fine spray under study. The computer sub-system processes the drops' sizes measurements obtained with the help of the diffraction measurement technique which scans the spray to produce a spatially resolved map of drops' size distribution.

Furthermore, the probing sub-system may be accommodated with a laser-based Particle Image Velocimetry (PIV) probing unit which scans for obtaining images of illuminated spray under study at interrogation stations of interest for measuring drops' velocities in the fine spray under study. The computer sub-system processes these images to produce spatially resolved characteristic velocities of drops.

The patternator unit includes an array of collecting tubes operatively coupled, at one end to the spray under study to collect water and a plurality of containers, each coupled to another end of a respective collecting tube, as well as a monitoring unit for monitoring water level change in the containers to measure the level change time rate. The monitored time rate of the water level change in the containers is processed by the computer sub-system to obtain volume flux distribution of the spray under study.

In another aspect, the present invention represents a method for 3-Dimensional (3-D) characterization of a near-field spray produced by a nozzle of interest. The subject method comprises the following steps:

(a) forming a Spatially-resolved Spray Scanning System (SSSS), which would include:

a control sub-system, nozzle rotating sub-assembly coupled to the nozzle under study to rotate the nozzle under study in accordance with commands issued by the control sub-system, a patternator sub-system disposed in a closed proximity to the nozzle opening and configured for measuring volume flux distribution at a predetermined radius of the spray in the plane orthogonal to the nozzle's axis, and a number of laser-based probes, each being of a predetermined configuration and operating based on specific physical principles to measure drops' parameters in the spray. The probes are operatively coupled to the spray of interest and are displaceable under control of the control sub-system with regard to the spray for sampling the area (volume) of interest to completely cover the region of interest.

Each probe unit would include a laser sub-system and a high speed camera sub-system operatively coupled to the control sub-system for the controllable actuation of the scanning operation.

The method continues through the steps of:

initiating the spray;

displacing the nozzle azimuthally in a controlled fashion, actuating the laser and the camera in accordance with the probe scanning operation; and measuring the volume flux distribution tracked back to the azimuthal displacement of the nozzle under study, and drops related parameters through scanning the spray of interest with the laser-based probes in synchronism with the azimuthal displacement of the nozzle under study.

Upon obtaining the measurement data, entering the measured flux distribution and drops related parameters of the spray, as well as the azimuthal displacement data into the computer sub-system configured to process the measured data in accordance with a measurement analysis algorithm and post-processing algorithms to create spatially resolved spray characteristics.

The subject method further comprises the step of applying basis functions compression to the spatially resolved spray characteristics to generate a compact representation of the spray.

During the scanning of the spray with the laser-based probes, the subject method is carried out through:
directing the pulsed laser beam onto the spray,
focusing the digital camera on the spray,
synchronizing the pulsed laser and the digital camera actuation to acquire double images of drops in the spray of interest separated by a predetermined image separation time interval,
applying spatial calibration and image processing to the double images of drops to result in drops' sizes in each double image, and
acquiring drops' velocities through comparison of drops' trajectories obtained from the double images and the image separation time interval.

In the subject method, the laser based shadowgraphy measurements may be applied to the spray containing drops ranging in size from 0.1 mm to 10 mm to measure spatial distribution of drops sizes, number and velocity;
laser-based diffraction imaging may be applied to the spray under study containing drops ranging in size from 0.1 μm to 100 μm to measure number and size of the drops; and
laser-based Particle Image Velocimetry (PIV) may be used to measure drops velocities in the spray under study, where the drops range in size from 0.1 μm to 100 μm.

As a result of traversing the probes with regard to the spray to the interrogation station(s), and rotating the nozzle in a controlled fashion, it is possible to track the measured data to sampling locations and azimuthal displacement, and to form an extended spherical interrogation region covering multiple imaging areas, each azimuthally aligned with predetermined interrogation stations.

Individual images of the multiple imaging areas can be combined. Measuring flux of distributions, drops' size distributions, and drops' velocity distributions in the spray under study are azimuthally correlated with the nozzle rotation, and the spray configuration can be transformed into a compact description through the steps of:
generating analytical functions describing spatial variation of the drops' density, size, and velocity in correspondence to an elevation angle, where the analytical functions include Legendre polynomials, Gaussian functions, and Fourier series, each defined through respective coefficients determined by processing the measured spray characteristics. The respective coefficients provide average values and profile shapes for the measured spray characteristics, for the Legendre polynomials and Gaussian functions, and the respective coefficients are determined from the nozzle geometry for the Fourier series.

As the result of measurements and data processing, the subject method is designed to generate a product database for the nozzle under study, followed by incorporating the product database into a suppression system design system.

The method further includes the steps of:
measuring azimuthally variable characteristics of the spray under study, and
applying Fourier series to the measured azimuthally variable characteristics to calculate a continuous interpolation function between the characteristics measured for adjacent spaces and tines formed in the nozzle's deflector.

These and other features and advantages of the present invention will be apparent from the following detailed description taken in conjunction with accompanying Patent Drawings.

BRIEF DESCRIPTION OF THE DRAWINGS

FIG. 6A represents elevation angle basis functions, and FIG. 6B represents azimuthal angle basis functions;

DETAILED DESCRIPTION OF THE PREFERRED EMBODIMENTS

Figure 1A:
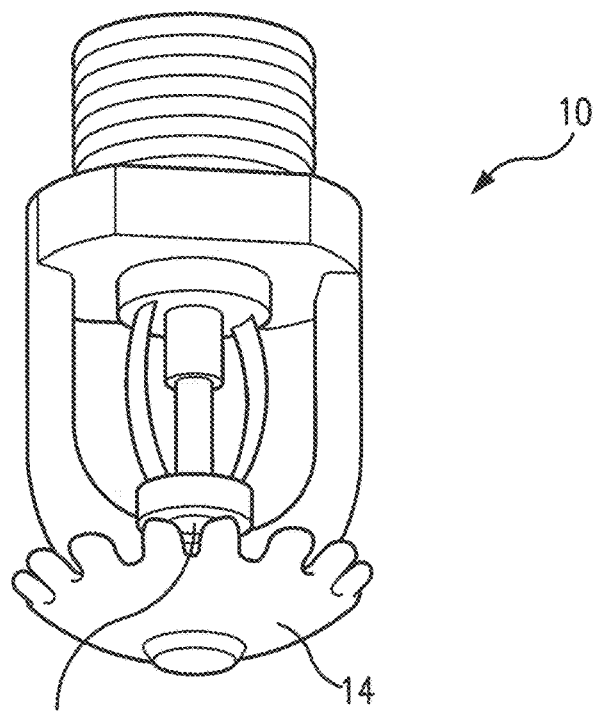
FIGS. 1A-1B illustrate a commercial sprinkler structure (FIG. 1A), and principles of the atomization process (FIG. 1B)
Figure 1B:
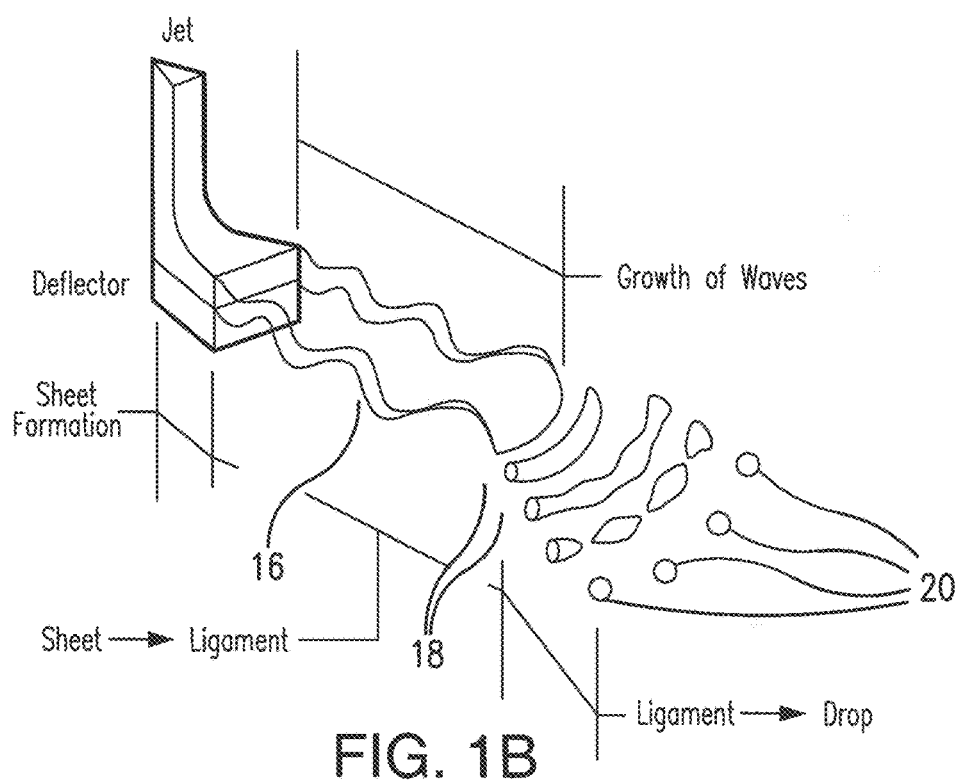

The present system and methods are built on principles of a hybrid approach where first principle VOF (Volume of Fluid) based CFD (Computational Fluid Dynamics) analysis is used to determine the flux distribution of the streams generated on the deflector surface (before atomization occurs), while a physics based model would be used for determining the flux distribution of the initial spray (just after atomization is complete) based upon input from the deflector simulation. This hybrid approach removes the need to resolve the smallest length scales associated with drop formation, while reducing the overall grid dimensions required.

Preliminary VOF (Volume of Fluid) simulations have been conducted with success to predict the formation of the tine and slot streams on the deflector.

Some initial photographs of the stream behavior very close to the nozzle have also been acquired with fast photography to provide a qualitative view of the flow in the spray formation region between the deflector and the initial spray (i.e. the atomization region).

The subject Spatially-resolved Spray Scanning System (SSSS) fitted with the patternator probe disposed at different radial stations close to the sprinkler (also referred to herein as a nozzle) plays an important role in actually quantifying the evaluation of the flux distribution from a position close to the deflector (r=0.05 m) to the initial spray location (r=0.35 m). In this region, the patternator probe is considered to be one of the best option, since the spray is not well formed making it impossible to perform drop measurements, which require discrete spherical shapes for sizing. These flux distributions can provide valuable data to support the establishment of physics based models to predict spray behavior at the initial spray location informed by first-principle simulations of flow along the deflector surface.

Spray nozzles (regardless of the application) fundamentally create 'slender' flow streams in the form of jets and sheets to facilitate atomization. The subject system and method operates spray initiation in 'slender' flow streams through highly-resolved observation, measurement, and analysis.

The subject Spatially-resolved Spray Scanning System (SSSS) provides unprecedented spatial resolution of the initial spray through field measurement, scanning, and data analysis techniques to produce descriptions of the spray, which are both highly detailed (for CFD integration) and physically meaningful (for engineering insight). The system can measure sprays with drop sizes spanning five decades (100 nm-10 mm scale) for use with a variety of applications.

As an example, the following description will be focused on sprays characterization for specific applications in fire suppression systems. However, the principles presented in the present Patent Application are envisioned to be fully applicable to any spray producing system.

The fire suppression performance of the sprays generated from sprinklers is determined by their ability to penetrate the fire to reach burning surfaces below, while dispersing water throughout the heated fire environment area. Spray penetration and dispersion are governed by the initial drop size and velocity characteristics of the spray, which depend on the injection conditions and sprinkler configuration.

In the subject methodology, the initial spray is fully characterized through a scanning technique using laser-based Shadowgraphy, Particle Tracking Velocimetry (PTV), and diffraction probes combined with volume flux measurements. This produces a vast quantity of simultaneous drop size/velocity realizations for each sprinkler spray. Near-field spray characteristics are established from highly resolved direct visualizations of sprays details and local measurements, which are subsequently mapped in spherical coordinate system consistent with the kinematics of the spray.

A data compression scheme is introduced which generates analytical functions describing the sprinkler spray based on the measurement data. These analytical functions are useful for initiating the sprinkler spray in computational fluid dynamics (CFD) based spray dispersion and fire suppression modeling. The framework of the present invention reveals physical characteristics of the initial spray not easily recognized from raw data.

The near-field spray measurements and associated data compression approach are validated by comparing volume density measurements below the sprinkler with volume density predictions generated from spray dispersion calculations initiated with the analytical spray functions.

In the present system, detailed measurements have been conducted near the sprinkler discharge, i.e., the near field measurements, to characterize the initial sprinkler spray. The comprehensive framework presents detailed measurements in a compact format for spray analysis and modeling. This framework provides the opportunity to establish a high fidelity spray initiation database, at least of the most popular sprinkler models, useful for widespread and consistent sprinkler dispersion and fire suppression analysis.

The SSSS of the present invention uses laser based diagnostics, image acquisition approaches, and control systems to manage vast quantities (~100 GB/360° scan) of spray information for subsequent analysis and processing.

Image processing provides three-dimensional maps for a complete description of the initial spray (drop size, number, and velocity), while a basis function based compression technique provides a compact (~50 coefficients/360° scan) physically rational description (describing millions of drop realizations) of basic spray characteristics.

The spatial resolution of the SSSS reveals spray details associated with injection conditions (including nozzle geometry) to improve nozzle designs, atomization modeling concepts, and engineering analysis of spray intensive systems.

The measurements and basis function approach underlying the operation of the present system provide means of generating the spray in fire suppression applications, which was not possible in prior systems where flux measurements from water collected at floor level were used as a reference, and near-field spray details (i.e. at the nozzle) were adjusted until dispersion predictions provided fluxes that matched the reference measurements. This crude approach, although producing valid fluxes at the floor, left the initial sprinkler spray largely unknown yielding little confidence in dispersion predictions in other configurations (e.g. with a challenge fire) outside the reference calibration.

The subject SSSS provides the ability to produce a standard sprinkler database for describing engineering spray characteristics (e.g., spray angle and drop size), while, at the same time, providing all of the spatial details necessary for generating the spray in fire simulations. The ability to specify the initial sprinkler spray is important to advance fire sprinkler technology and fire suppression system design beyond empirical 'cut and try' development approaches and code based system design.

Moreover, the SSSS has been developed as a new standard for not only evaluating, but also for application specific commercial qualification of sprinkler sprays based upon their characteristics, namely including drops' size, flux, and spatial uniformity.

Figure 2:
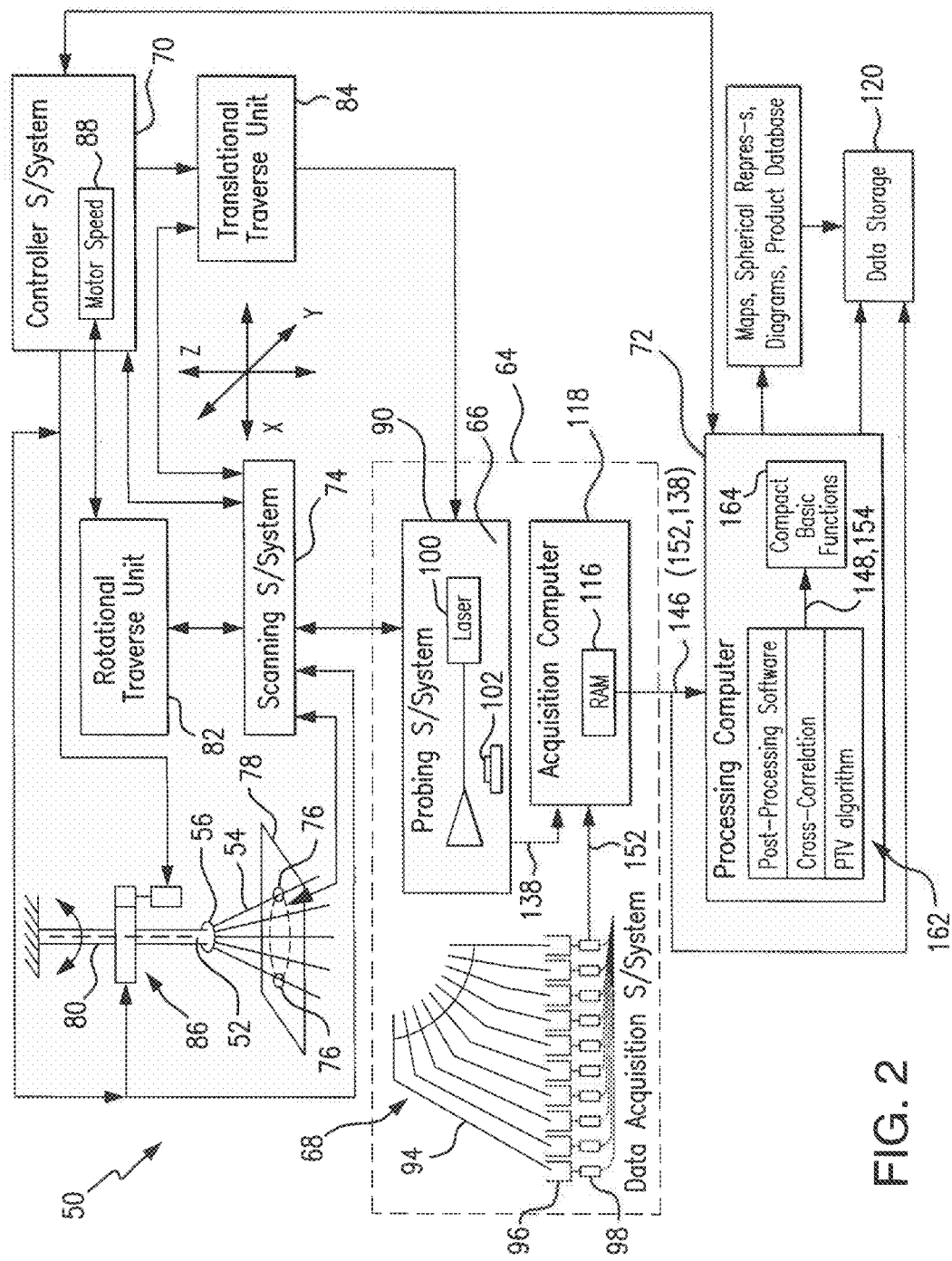
FIG. 2 is a schematic representation of the Spatially-resolved Spray Scanning System (SSSS) of the present invention.
Figure 7:
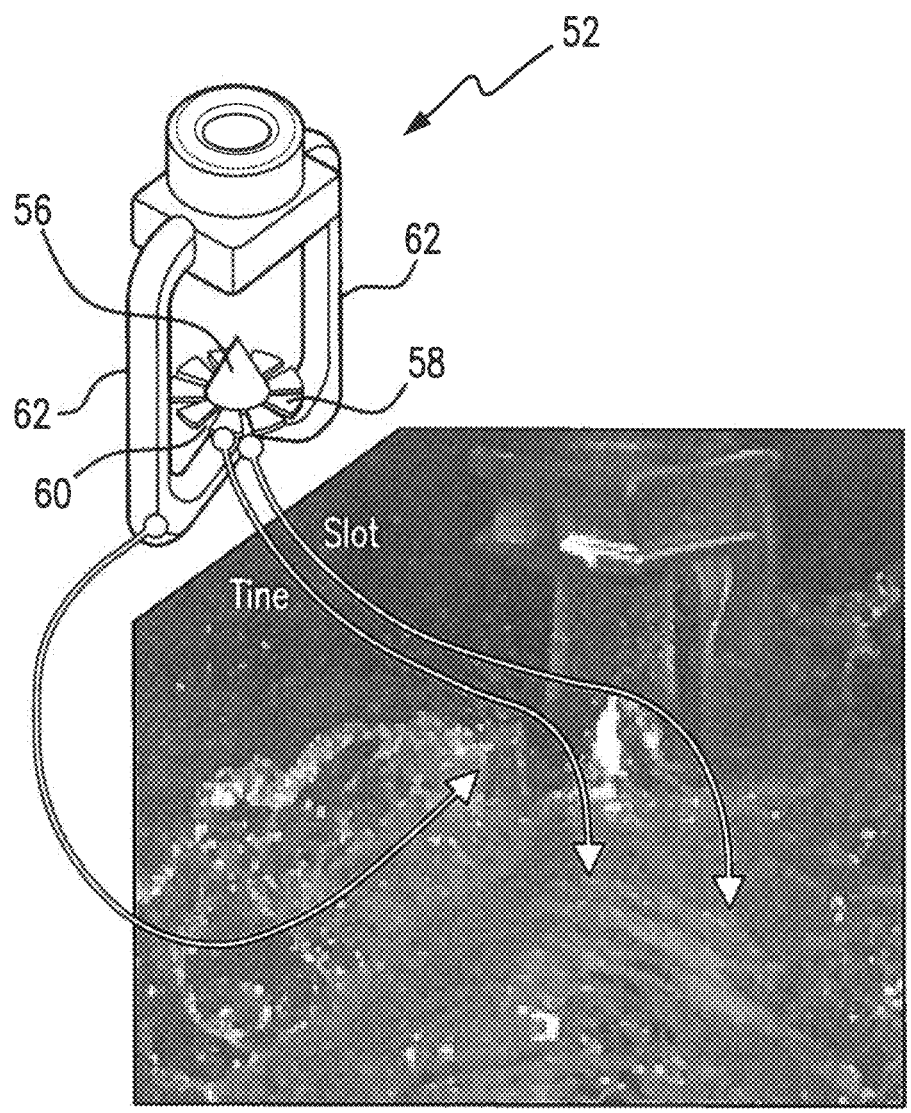
FIG. 7 is a representation of the streams generated along the deflector of the nozzle of interest.

Referring to FIG. 2, a Spatially-resolved Spray Scanning System (SSSS) 50 of the present invention performs mechanical patternation to measure flow/flux distribution combined with laser-based diagnostics for measuring drop sizes and velocity. In the system 50, the sprinkler (also referred to herein as a nozzle) 52 font's a spray 54 of a liquid, for example water. The sprinkler, as best shown in FIG. 7, is equipped with a sprinkler deflector 56 which has a plurality of tines 58 and spaces (slots) 60, and a frame, i.e., two frame arms 62, which provide the structural component which holds the sprinkler together and supports the deflector during water discharge.

A water supply pipe (not shown) is connected to the sprinkler at the base of the frame to be supplied with water from a water reservoir with the help of a pump (not shown). A flow meter and pressure transducer are provided for operation conditions measurements. Acrylic splash guards are provided to prevent the fluid dispersion beyond a specific area to prevent exposure of equipment to water.

A laser and a digital camera are used in measurement scheme as will be presented in further paragraphs.

In experiments, several designs of sprinklers were used in measurements, to generate unconfined sprays characterized by the subject methodology.

The system 50 of the present invention includes a data acquisition system 64 which incorporates a probing sub-system 66 and a mechanical patternator sub-system 68, both operatively coupled to the spray 54.

A control sub-system 70 and a processing computer sub-system 72 for data reduction, data processing, and coordinating the operation of all sub-systems of the SSSS 50 are included in the subject system and operate as will be detailed in following paragraphs.

The data acquisition sub-system 64 is also equipped with a scanning sub-system 74 which is activated by the control sub-system 70 under the control of the processing computer 72 to provide a complete scan of the spray under study.

The spray 54 is characterized at a number of azimuthal stations (areas) 76, also referred to herein as interrogation (or assessment) stations. The interrogation stations may be located at specific coordinates with regard to the spray. For example, the interrogation stations 76 may be arranged at one (or a plurality) of orthogonal planes 78 spaced "vertically" along the axis 80 of the nozzle 52. At each orthogonal plane 78, the interrogation stations 76 may be given specific azimuthal coordinates with regard to the spray or the nozzle.

The simple action of rotating the nozzle 52 following the natural coordinate system of the spray under study creates an opportunity to address the spatial resolution challenge. The scanning sub-system 74 is built with a rotational traverse unit 82 that would slowly (~0.03 RPM) rotate the spray generation device (i.e., nozzle) 52, and a translational traverse unit 84 that would quickly move the probing sub-system 66 to the appropriate interrogation station(s) for sampling the spray 54 in one (or a number of) the orthogonal plane(s) 78 when necessary, i.e., when multiple interrogation (or probing) stations 76 are required to cover the entire region of interest in the spray under study.

The spray scanning principles underlying the functionality and operation of the subject system facilitate the highly spatially-resolved acquisition of measurement data characterizing the spray under study. The probing technology employed in the SSSS equipped with the scanning capabilities provide direct visualization of spray details with unprecedented spatial resolution.

Specifically, the scanning sub-system 74 includes a motor and gear assembly 86 schematically shown in FIG. 2 for rotating (azimuthally displacing) the spray nozzle 52 under the control of the control sub-system 70 represented by the motor speed controller 88 operatively connected to the motor and gear assembly 86. The control sub-system 70, as well as the motor and gear assembly 86, and the motor speed controller 88, operate in accordance with instructions issued by the computer 72.

Another part of the scanning sub-system 74, i.e., the translational traverse unit 84, may include a platform 90 supporting the laser-based probes. The translational traverse unit 84 is capable of delivering the probing sub-system 66 to the interrogation station(s) 76 in the area of interest for detailed scanning of the spray 54 in accordance with instructions received from the computer 72. The platform 90 is envisioned for translation in X-Y-Z directions (as well as angled displacement) with regards to the nozzle 52, i.e., covering different positions along the nozzle 80, and can be displaced azimuthally within the orthogonal planes 78 (perpendicular to the axis of the nozzle) in order to sweep through the entire region of interest, i.e., scanning through the entire near-field spray.

In each orthogonal plane 78, one or a number of interrogation stations 76 may be required for scanning the entire near-field spray. In order to cover the entire region of interest, the platform 90 can be moved towards the respective interrogation station and subsequently moved between different interrogation stations of interest, as well as changing the position of the probe delivered to the interrogation station, under the control of the computer 60, supported by the control sub-system 70 actuating the motion of the platform 90.

Figure 8:
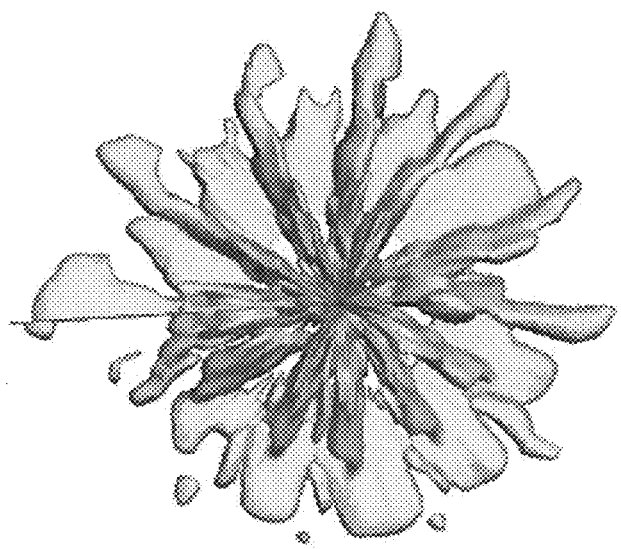
FIG. 8 is a representation of a bottom view of the sprinkler flux iso-contour obtained at ~0.02 m from the sprinkler's centerline.

This scanning technique sweeps out a surface (or volume) of the spray depending on the probe configuration. As shown in FIG. 7, the near-field scan measurements acquired by the SSSS 50 permits a direct visualization of the thin streams generated along the deflector 56 characterizing the spray interaction with the three-dimensional structure of the sprinkler having tines 58, spaces 60, and frame arms 62. A bottom image of the flux iso-contour acquired at ~0.02 m from the sprinkler centerline is illustrated in FIG. 8.

Figure 3:
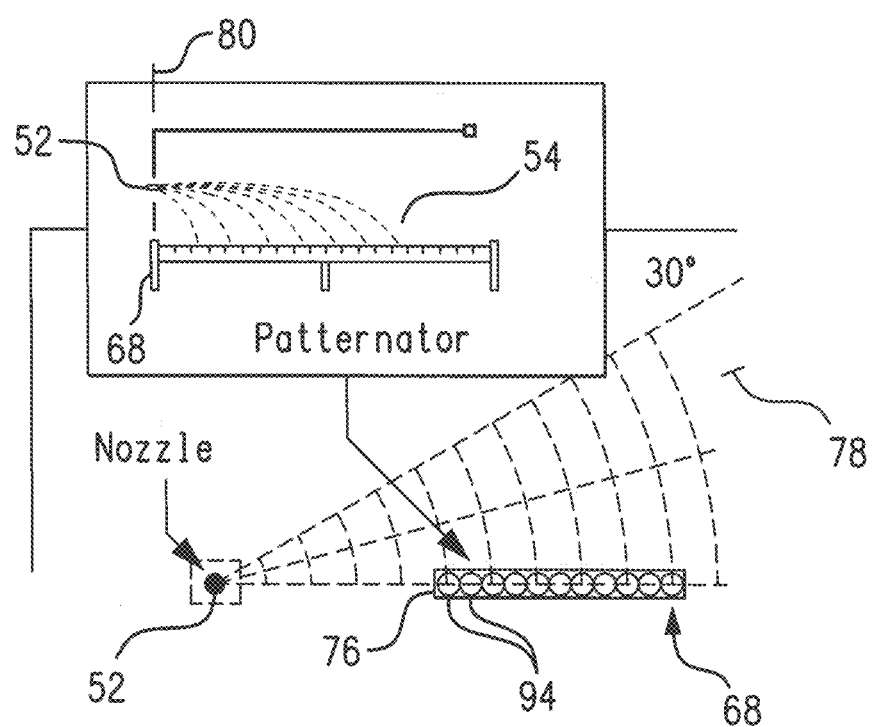
FIG. 3 is a schematic representation of the experimental setup using the mechanical patternator in the SSSS of the present invention.

The data acquisition sub-system 64 includes a mechanical patternator sub-system 68 which is used to measure the water flux distribution in the spray 54. As schematically presented in FIGS. 2-3, the patternator probe 68 is disposed at a predetermined distance from the nozzle to provide water flux distribution at a predetermined radius in the orthogonal (r-θ) plane 78 as the nozzle 52 is rotated azimuthally (ψ). The spatial resolution of the patternator probe technique is unprecedented and periodic details associated with the sprinkler geometry are readily apparent including important deviations from the periodicity due to the sprinkler frame arms.

The patternator probe 68 is positioned radially in the orthogonal plane 78 of interest to collect water through a series of collecting tubes 94 which may be arranged in an arch-like array, as shown in FIG. 2. Water of the spray 54 produced by the nozzle 52 fills containers 96. The water level of the water in containers 96 is monitored continuously with transducers 98. The volume flux 152 is determined from the measured time rate of the water level change in the containers 96.

Figure 9:
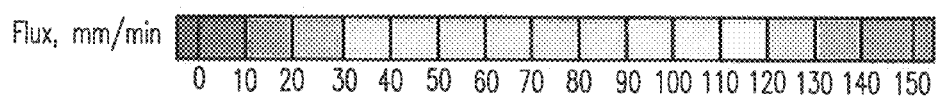
FIG. 9 is a spherical representation of measurements of flux distribution in the system of present retention.
Figure 9:
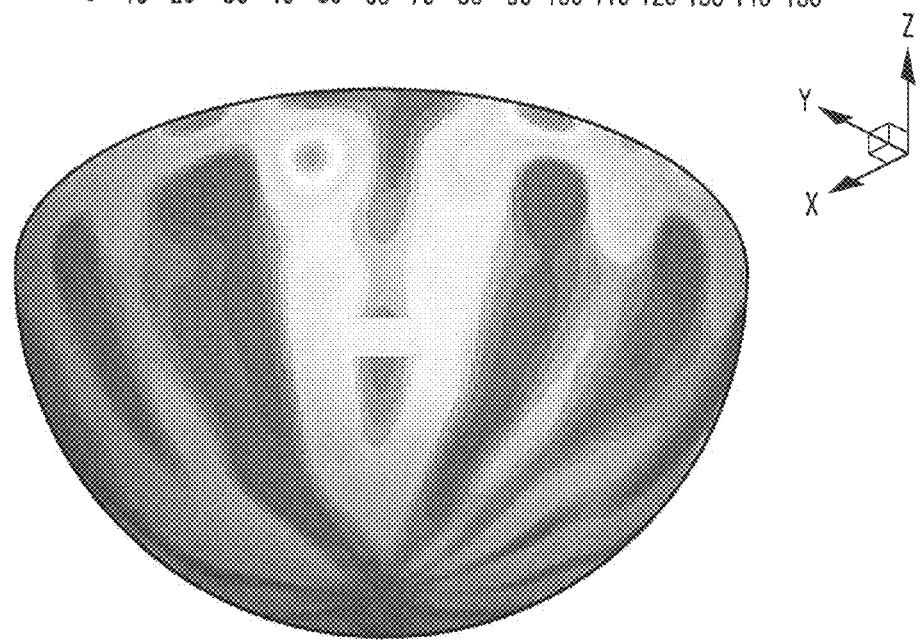

Simultaneously the azimuthal location (ψ) of the nozzle 52 during the spray's flux measurements is known based upon its rate of rotation. The computer 72 processes the volume flux measurements, and the azimuthal readings to generate flux distribution which are mapped to the area (volume) of interest in the spray. FIG. 9 shows the flux distribution acquired through the use of the patternator 68 and arranged to map out a hemisphere in proximity to the nozzle (r=0.05 m) even before atomization is completed.

The flux distribution is an important quantity in nozzle performance because it has a first order impact on the dispersion of the spray. It is also useful to compare the fluxes from mechanical patternation measurements with drops sizes, quantities, and velocities obtained using combined measurements by the laser-based probes provided in the probing sub-system 66 of the subject SSSS 50, including Planar Imaging (e.g., Particle Image Velocimetry), Shadowgraphy, Diffraction, etc., shown in FIG. 4.

For example, the flux measurements 152 obtained from the patternator probe unit 68, may be compared with Shadowgraphy/PTV (Particle Tracking Velocimetry) measurements in coarse sprays (with the drops sizes in the range of 0.1-10 mm) for validation. In fine sprays (with the drops sizes in the range of 0.1-100 μm), the diffraction technique may be used for drop size and number density, while the PIV (Particle Image Velocimetry) technique may be used for drop velocity measurements.

The patternator 68 provides flux measurements 152 useful for estimating drop size/velocity correlations needed for a complete description of the spray (as these quantities are measured independently). It is recognized that Phase Doppler Particle Analyzer (PDPA) systems are often used in fine sprays to obtain simultaneous measurement of drop size and velocity and thus intrinsically correlating these quantities. However, the small probe volume (~2 mm) is prohibitively small for some of the large-scale spray applications of interest for the SSSS.

The probing sub-system 66 is based on interaction of a laser beam with the spray, and may include multiple probes available for the SSSS 50 depending on the drop size (course spray, e.g., 0.1-10 mm; or fine spray, e.g., 0.1-100 μm) to obtain the set of measurements required for complete description of the initial spray.

The probes are easily moved to sweep out hemispheres of different radii or different configurations all together depending on the spray of interest.

The probing sub-system 66, as shown in FIG. 2, uses a laser source 100 and a digital camera 102 to operate in accordance with physical principles underlying functionality of each laser-based probe 104 available for the required spray measurements.

Shadowgraphy

Figure 4:
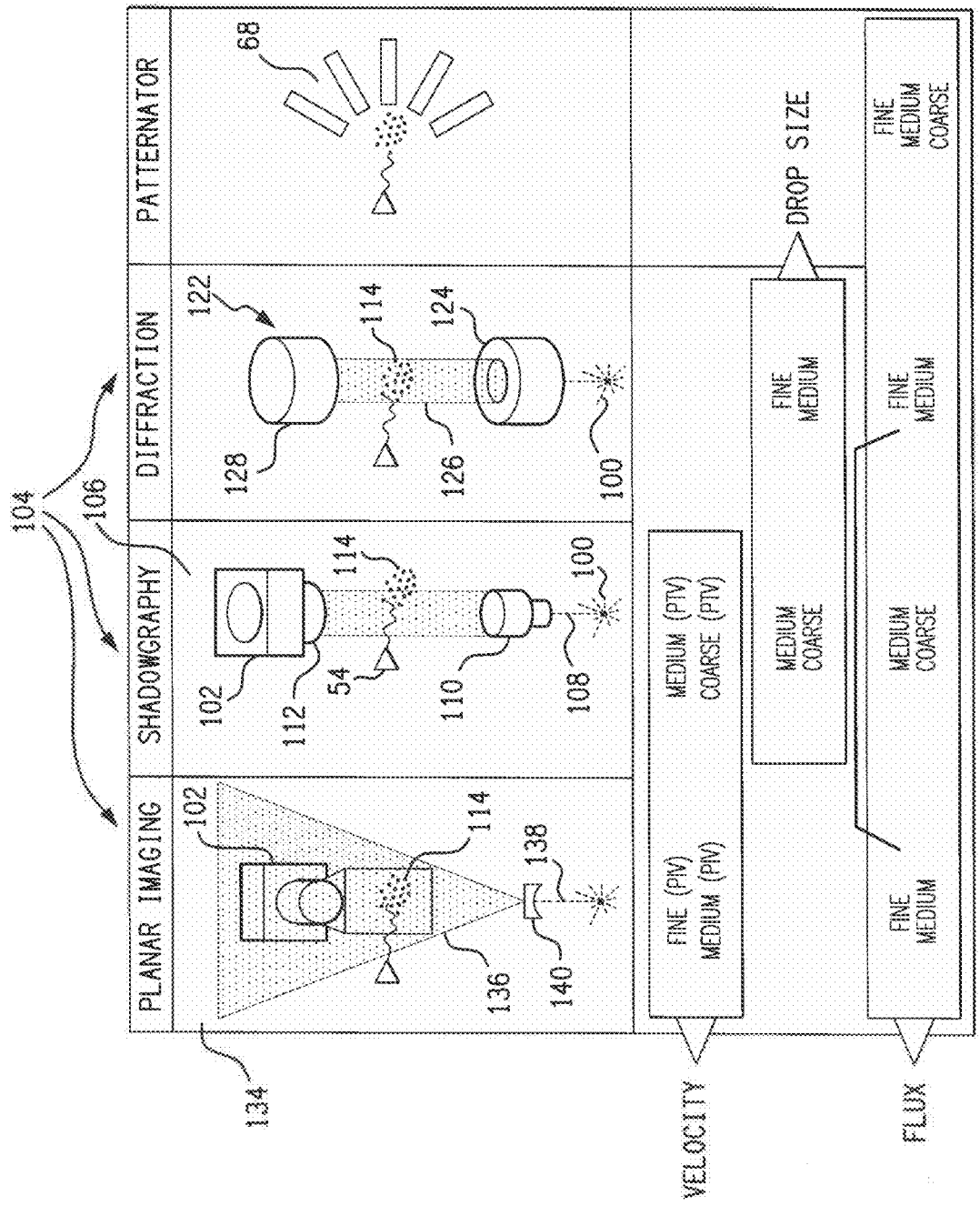
FIG. 4 is a schematic representation of laser-based probe options for the SSSS of the present invention.

As shown in FIG. 4, in addition to the patternator 68, a variety of probes 104 are used as a part of the probing sub-system 66 for complete scanning and characterization of the near-field spray 54 produced by the nozzle 52. A commercial Shadowgraphy sub-system 106, for example, a LaVision shadowgraphy unit, may be employed for coarse sprays for providing spatial distribution of drop size, number, and velocity.

The shadowgraphy probe 106 uses a high-energy dual cavity pulsed laser source 100, for example, Nd:YAG laser, to generate visible light 108 (~30 mJ/pulsed of 532 nm) over a relatively large diffuse background (~0.2 m) created by high efficiency Diffuser optics 110. The shadowgraphy probe sub-system 106 also uses a synchronized high-speed high-resolution digital camera 102.

In experimentation, a 4 MP digital camera fitted with a 50 mm Canon f/1.4 lens was aimed at the illumination field and focused approximately 100 mm in front of the Fresnel lens producing a 150 mm square field of view with a depth of field of approximately 28 mm.

The sprinkler spray 54 was directed in front of the illumination field and through the camera's imaging region partially blocking the light received by the camera and producing distinct shadow images of drops. The pulsed laser and camera were synchronized to provide double images of the drops separated by a short time interval (~60 μs). The imaging optics 112 are oriented such that drops 114 pass between the background illumination and the camera casting shadows.

The short light pulse (~10 ns) produced by the laser 100 freezes the motion. By spatially calibrating the camera's field of view, the drops' sizes are easily determined using an edge detection algorithm. The ability of the dual cavity laser to double pulse over a short time delay (~0.1 ms) allows for displacement and ultimately velocity measurement of the drops' shadows imaged by the camera using a Particle Tracking Velocimetry (PTV) algorithm. The high frequency laser light source (up to 100 Hz) provides an opportunity to generate large amounts of data for stationary statistics relatively fast.

In experimentations, spatial calibration and image-processing were applied to provide the drop sizes in each image. The drop velocities were determined through comparison of drop trajectories obtained from image pairs and the image pair separation time. Two hundred image pairs were obtained providing hundreds of thousands of simultaneous drop sizes and velocities at a given imaging station (i.e., 150×150×28 mm imaging region).

The sprinkler was traversed and rotated to sweep out a large spherical interrogation region (from multiple imaging stations) extending radially between approximately 100 mm and 400 mm. These imaging stations (areas) were azimuthally aligned with the tine and space features of the deflector. The measurement regions were rotated about the axis of the sprinkler assuming rotational symmetry and neglecting frame arm effects to visualize the sprinkler spray.

Figure 10:
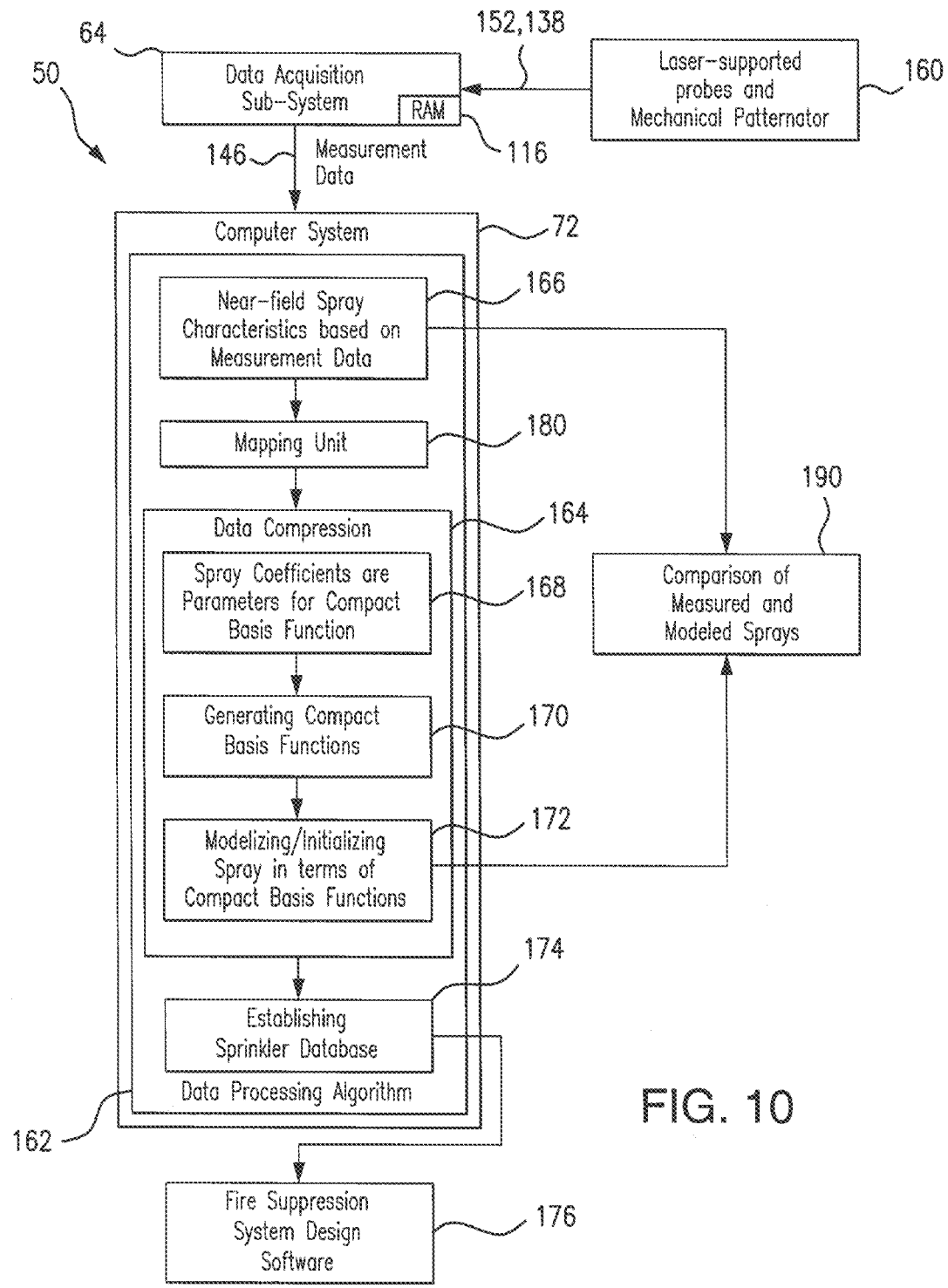
FIG. 10 is a flow chart diagram of the process underlying the operation of the SSSS of the present invention.
Figure 11:
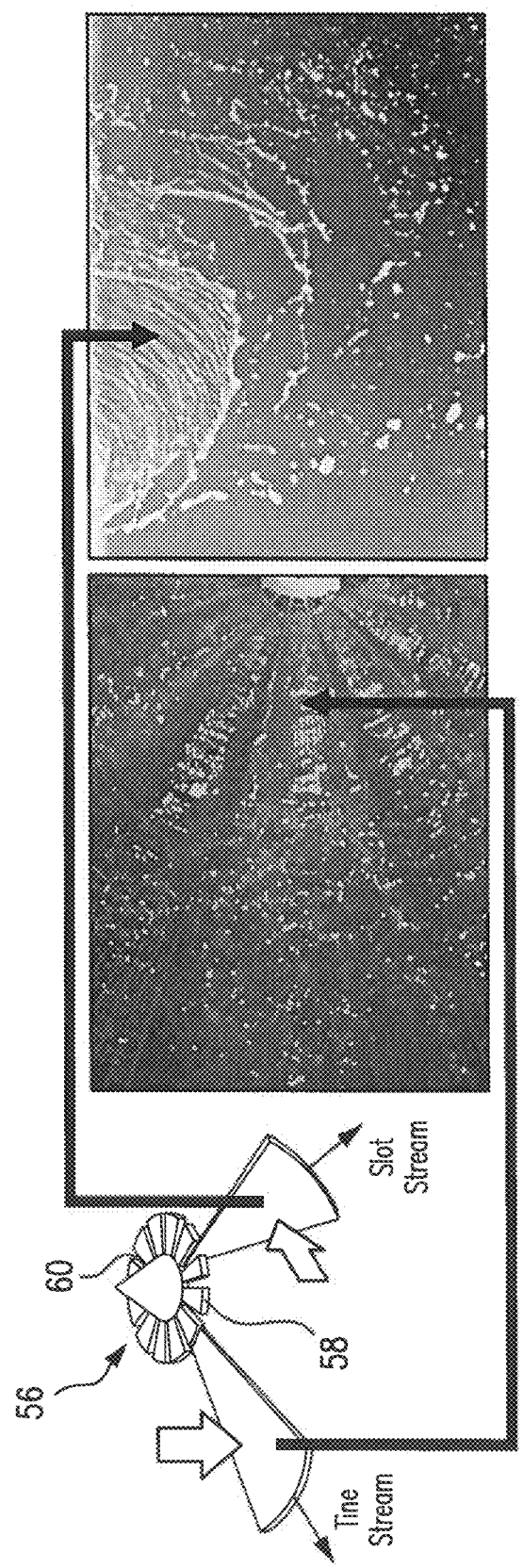
FIG. 11 is a representation of disintegrating streams generated by a commercial sprinkler.
Figures 12A, 12B:
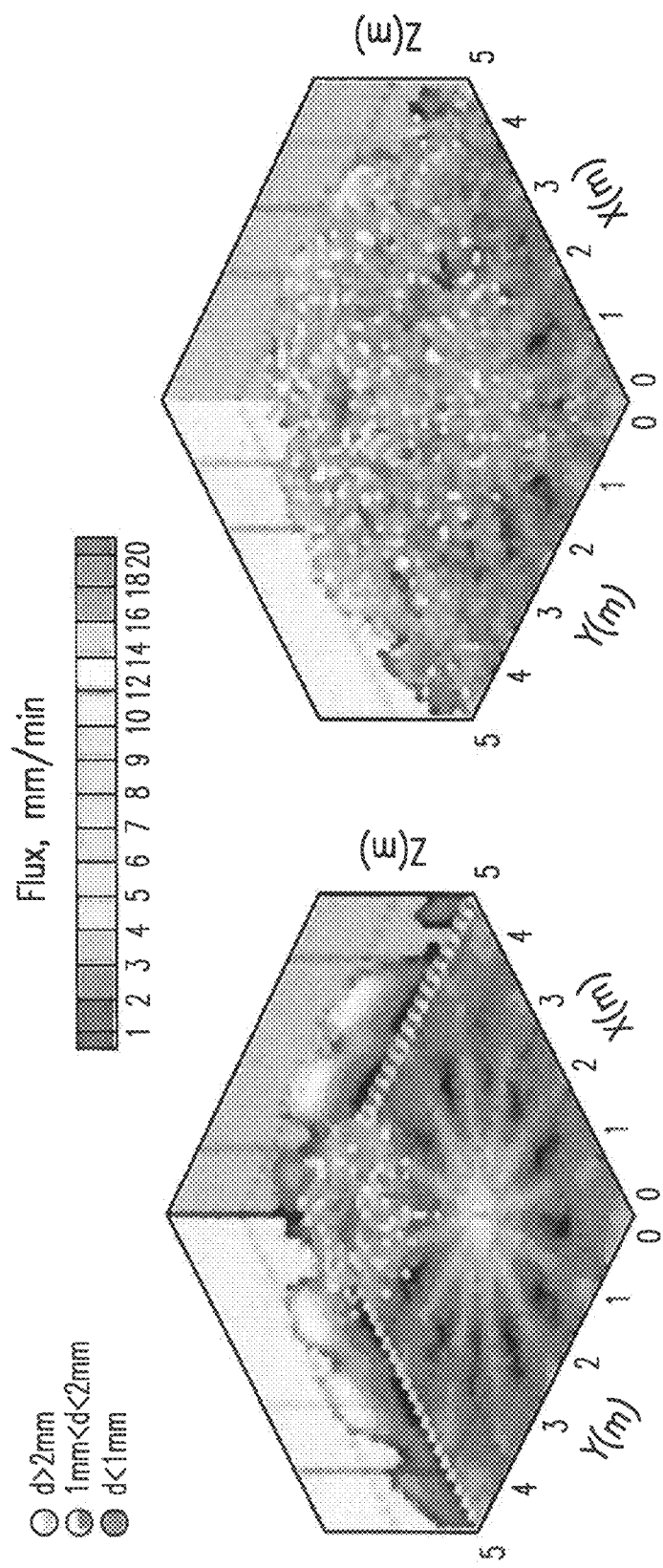
FIGS. 12A-12B represent diagrams of dispersion and surface wetting for the same commercial sprinkler based on preliminary measurements and the basis function initial spray data reduction framework, respectively.

The results 138 of measurements were entered into in the RAM 116 of the acquisition computer 118, and further supplied to the computer system 72 for further processing in accordance with the specifics shown in FIG. 10.

Figure 13A:
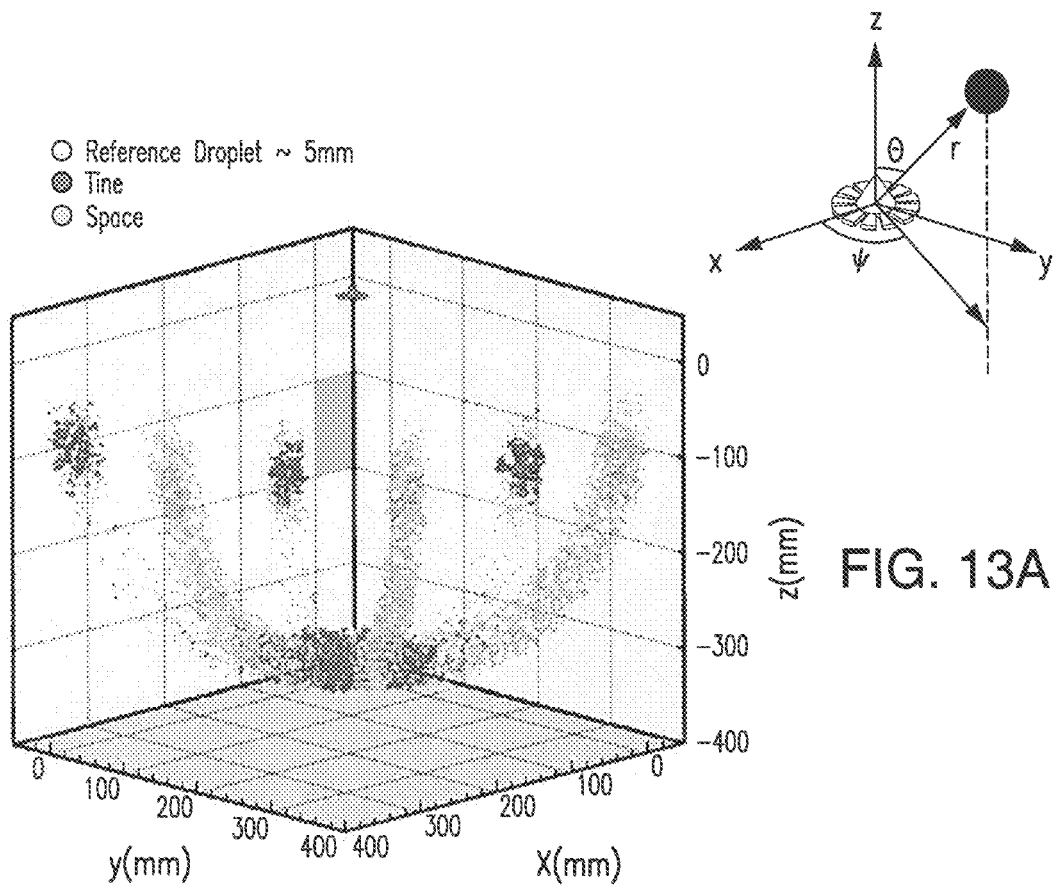
FIG. 13A is a diagram of drop sizes measurements aligned with the tines and slots.

FIG. 13A shows a reconstructed 3-D spherical view of the sprinkler spray based on the shadowgraphy measurements. After individual images and imaging stations are combined, the shadowgraphy measurements produced almost one million drop measurements at each test condition, providing a large sample for reliable statistics.

Shadowgraphy measurements suggest that only about 5 s at each interrogation station would be required for converged statistics in coarse sprays. Because of the large number of images collected over a relatively short time, fast digital storage is required for the shadowgraphy scans. The images may be held in the RAM 116 of the acquisition computer 118 (for example, 128 GB capable of storing over 50K images) during the scan. The images may be later written to a memory unit 120, such as for example, disks or solid-state data storage for post-processing, or transferred directly to the computer 72 for processing, as will be presented in detail infra.

Diffraction

The probing sub-system 66 used in the SSSS 50 may also use the Diffraction probe 122, shown in FIGS. 2, 4, and 5A-5B. A commercially available Malvern drop sizing system based on light diffraction principles may be used for counting and sizing drops in fine sprays. In the Diffraction probe 122, transmitting optics 124 are used to collimate a laser diode 100 (~12 mm diameter) creating a cylindrical measurement volume 126. Drops 114 entering the exposed portion of the sampling volume 126 diffract light at various angles according to their size. Receiving optics 128 are used to collect the diffracted light onto concentric detector rings 130 to measure the intensity distribution of the diffracted light. The intensity distribution over the concentric rings 130 is used along with derived correlations to calculate the drop size distribution. The entire signal is then focused onto a power detector 132, which measures attenuation of the incident light providing an estimate of the concentration. The measurement volume may be sampled (up to 10 kHz) and swept during the scan to produce a spatially resolved map of the drop size distribution.

Figures 5A, 5B:
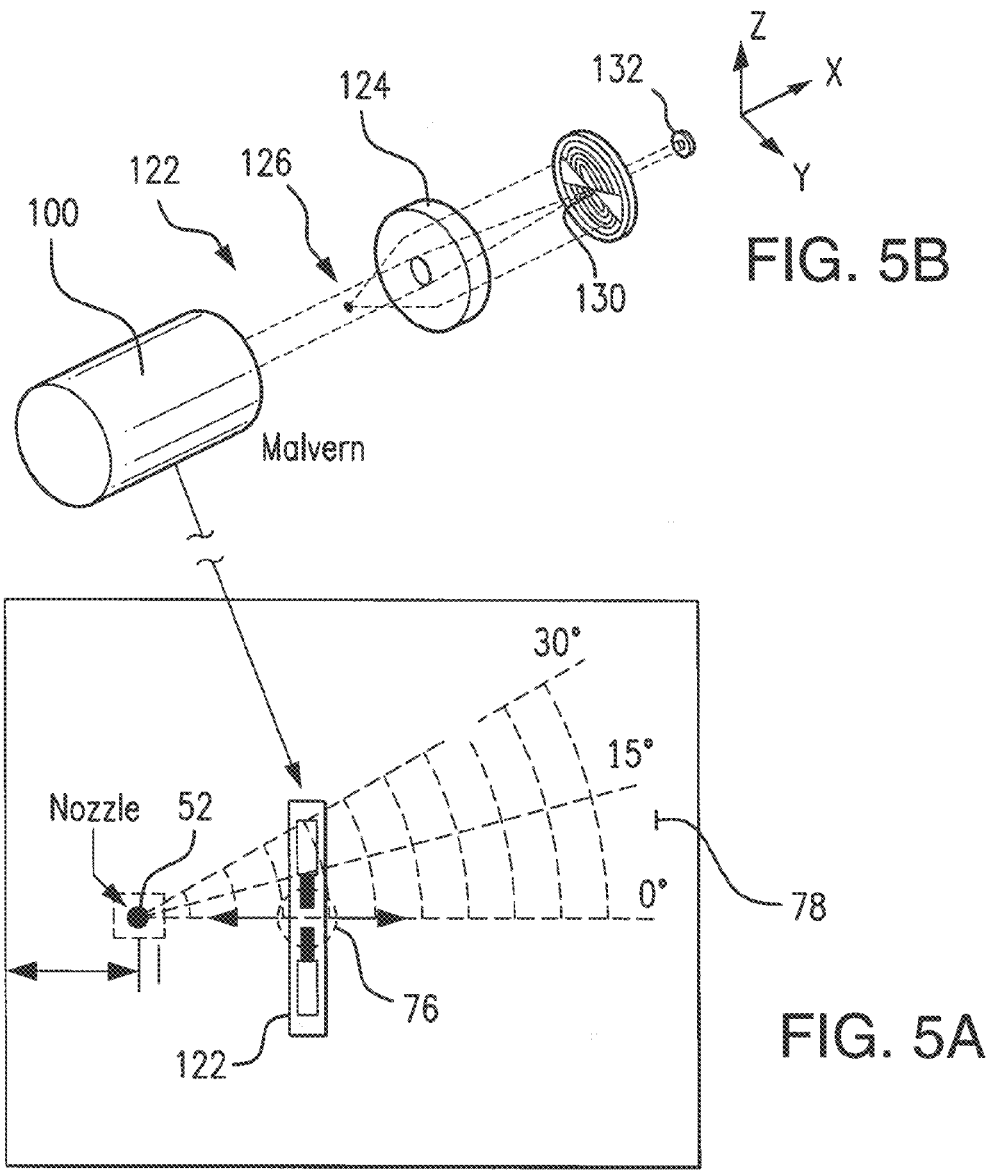
FIG. 5A is a schematic representations of the drop size measurement experimental setup using diffraction technique in the SSSS of the present invention.
FIG. 5B is a schematic representation of the laser-based diffraction probe.

As an example, FIGS. 5A-5B show, the drop size measurements based on scanning of the spray under study with the diffraction probe 122. Moreover, the experimental set-up shown in FIG. 5A, can be used in the system 50 for scanning/sampling routine using any of the probes of the probing sub-system 56 by moving the probe's optics to interrogation station(s) 76 of interest in an orthogonal plane 78 of interest by controlling the position of the platform 90 (shown in FIG. 2) which supports the probing sub-system 56 to scan the spray at the areas of interest.

Particle Image Velocimetry (PIV)

As shown in FIG. 4, the probing sub-system 56 includes a planar imaging probe 134. A commercially available LaVision PIV system may be used to measure velocities in fine sprays. In this technique, short duration (~10 ns) light sheets 136 are created by passing a laser beam 138 generated by a double-pulsed laser 100 through a cylindrical lens 140. The pulses of the laser are separated with a short time delay (~10 µs).

Drops 114 are illuminated as they pass through the light sheet 136. A high speed camera 102 is synchronized with the double pulsed laser 100 to capture the images of the illuminated spray. The images are divided into interrogation regions and the net displacement of particles within the interrogation regions is determined using a cross-correlation algorithm.

Velocities for each interrogation region are readily determined from the displacement and time delay providing spatially resolved velocity measurements. Although the velocities are spatially resolved, velocities of individual drops are not measured and only characteristic velocities of drops are available from the PIV measurement. Similar to the shadowgraphy and diffraction techniques, the PIV optics can be moved to multiple interrogation stations and scanned to sweep out large spray volumes. The fast laser and image acquisition system allows for converged statistics in a relatively quick manner.

As shown in FIG. 2, the raw measurement data 138 obtained by the probing sub-system, is saved in the RAM 116 of the acquisition computer 118.

The subject system 50 is capable of generating massive amounts of data associated with capturing the millions of drops generated by nozzles to form industrial sprays. As previously noted, large amounts of RAM 116 may be used to hold the data, cumulatively indicated as data 146, including both the patternator's measurements 152 and the laser-based scanning measurements 138, in the memory during scanning and flux measurements for later processing by the computer 72 or by any other processing means.

The acquisition of spray data and scanning procedure are also coordinated with the control sub-system 70 to ensure that the location of data sampling is tracked.

After the scanning routine is complete, a variety of data processing algorithms 162, for example, commercially available post-processing packages, may be used to convert the data acquisition results 146, such as, for example, the images in the case of the shadowgraphy and PIV probes, and intensity distributions in the case of the diffraction probe, into spray characteristics 148. In addition, the data processing algorithms convert the readings 152 from the pressure transducers 98 into the flux data 154.

After processing the raw measurement data 146 acquired by the data acquisition sub-system 64 into the spray characteristics 148 and flux data 154, a maximization of the utility of the SSSS is still required.

Figure 6A:
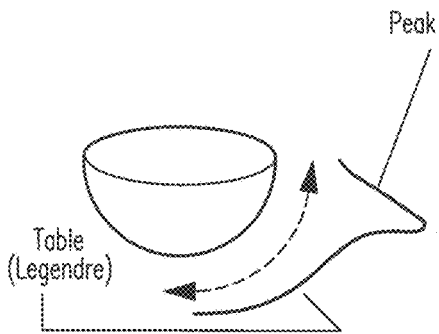
FIGS. 6A-6B represent application of Basis Functions for Data Reduction; where
Figure 6B:
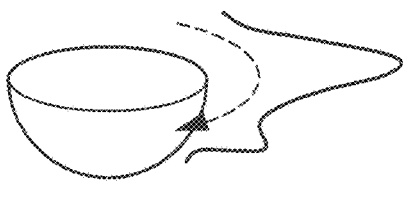

The SSSS 50 produces large datasets (through fast scanning) meeting the challenges of spatial resolution and converged statistics, while at the same time creating a data reduction challenge. The SSSS addresses data reduction through the use of basis functions to describe the spray measurements as shown in FIGS. 6A-6B. These basis functions not only reduce the data but also facilitate data interpretation with physically meaningful coefficients that are also capable of generating the stochastic spray for computational analysis.

For sprinklers in a spherical coordinate system, Fourier series (shown in FIG. 6B) are used to describe the azimuthal variation of stochastic spray properties. Gaussian functions and Legendre polynomials (shown in FIG. 6A) are used to describe elevation angle variation in stochastic spray behavior. Log-normal Rosin-Rammler distributions (shown in FIG. 6A) are also used to describe drop size distributions. The significant coefficients of these basis functions, presented in FIGS. 6A-6B, can be related to the characteristic physical quantities, including spray angle, tine/slot flow split, and characteristic drop size.

For different nozzles, other coordinate systems and basis function definitions may be appropriate. The use of Proper Orthogonal Decomposition (POD) approaches could also be explored, although POD approaches may make connections with physical characteristics of the nozzle or spray less obvious.

Referring to FIG. 10, which depicts, in a schematic functional format, the operation of the Spatially-resolved Spray Scanning System 50 of the present system, the data acquisition sub-system 64 measures characteristics of the spray of the sprinkler 52 under study using laser-supported probing sub-system 66 and patternator 68 and patternator methodologies schematically presented as block 160. Measurement data 152, 138 are obtained which characterize an initial spray, i.e. near field, of a sprinkler under study.

The measurement data (in the format of images acquired in the Shadowgraphy and PIV scanning, and light intensity distributions acquired during the diffraction probe scanning, as well as readings of transducers of the patternator probe) can be initially stored in the acquisition computer's RAM 116, and/or supplied, as measurement data 146 (cumulative of data 138 and 152) to the processing computer sub-system 72 which is configured to process the measured data in accordance with a data processing algorithm 162 designed specifically for the purposes and objectives of the present concept.

The algorithm 162 includes a data compression unit 164 which is configured to generate compact functions describing the sprinkler spray based on the measurement data as will be detailed in further paragraphs.

The algorithm 162 includes a near-field spray characteristics block 166 which, based on the measurement data, calculates the characteristics of the spray to provide its full description.

In the data compression unit 164, a calculation spray coefficients block 168 is coupled to the near-field spray characteristics unit 166 to calculate coefficients needed to generate compact basis functions for describing the spray.

The logic 162 of the present system further includes a block 170 generating analytical functions describing the spray in which the compact basis functions for describing the spray are generated based on the coefficients supplied from block 168.

A spray modeling unit 172 constitutes a portion of the data compression unit 164 and is configured to characterize the spray in terms of the compact basis functions generated in block 170 to create a product (sprinkler) database in block 174.

The basis compact functions generated in block 170 are used to provide a compact physics based representation of the spray that is suited for initializing the spray in computer simulations performed in block 172. The compact basis functions may be generated, for example, for specific fire suppression devices in order to create the product database in block 174. The database in block 174 may be incorporated into fire suppression system design software 176 so that designer would need no specific knowledge on a fire suppression device beyond the device name. The product database is a database of all data pertaining to a product, i.e., sprinkler, including technical specifications of the product, specifications for manufacture and development, types of materials that are required to produce the product, etc.

The measurement analysis software package, i.e., algorithm 162, used in the present system, has been developed to facilitate post-processing of the millions of drop measurements required to characterize the spray in terms of the basis compact functions. The algorithm 162, as well as the associated measurements, are important to the development of the product database in block 174.

The subject reduced physics droplet tracking method accounting for drag forces is capable of accurately predicting the dispersion of the fire suppression spray (after initiation described with basis functions and the product database) thereby greatly reducing the computation requirements for spray dispersion analysis. The reduced physics modeling approach can be incorporated into a game engine to develop fire suppression system design software for interactive real-time graphics based design and evaluation. Using interactive design software, the fire suppression system may be evaluated based on the volume flux measurements of water under quiescent conditions consistent with regulatory code requirements and fire protection engineering practices, which addresses automatic fire sprinkler systems design approaches, system installation, and component options to prevent fire death and property loss. A number of interactive fire suppression systems design software are available in the industry. They are known in the prior art and are not discussed herein in detail.

The present system is equipped with a mapping unit 180 configured to map the near-field spray characteristics in a spherical coordinate system consistent with the kinematics of the initial spray.

Various parameters of the spray were calculated from the measured data, as presented infra.

Volume Density

Radial volume density distributions were obtained using the mechanical patternator positioned below the sprinkler deflector and aligned azimuthally with the distinct tine and space features of the deflector. A characteristic dispersion length scale, R, first introduced by Prahl and Wendt in [J. M. Prahl, et al., Fire Safety J. 14 (1988) 101-111], was employed to facilitate analysis of the measurements. This reference quantity provides a maximum radial location that the spray can reach without air friction, and is given by $$R = U(2h/g)^{1/2} \quad \text{(Eq. 1)}$$

where h is the measurement elevation below the nozzle, g is the gravitational constant, and U is the maximum initial spray velocity.

The resulting volume density distributions in the r'=r/R coordinate describe the relative effect of drag on dispersion. The dimensionless linear density of dispersed volume flow, q', is given by $$q' = \frac{q''}{Q/\pi R^2}(2r'), \quad \text{(Eq. 2)}$$

where q″ is the area volume density and Q is the nozzle flow rate. The linear density provides a measure of volume flux weighted by the radius taking into consideration that more volume is captured by the larger area as the radius is increased.

Spray Initiation

These critical quantities for spray initiation are available from stochastic analysis of the measurements. It is daunting to consider the task of characterizing these sprays by tabulating measurements from individual sprinklers at every operating condition. However, a detailed analysis of the measurements reveals that a more compact representation of the initial spray is possible.

The computer system 72 of the present invention is provided with the Data Compression sub-routine 164 depicted in FIGS. 2 and 10 for compressed formulation which facilitates generalization over changes in operating conditions and nozzle geometries.

The initial sprinkler spray may be completely characterized in terms of the following quantities: drop location (radius, elevation angle, azimuthal angle), drop velocity, drop diameter, and drop density available from stochastic analysis of the measurements acquired in measurement sub-system. Although a formidable task, initialization tables for these quantities can be generated for individual sprinklers at various operating conditions. However, a more compact representation of the initial spray attained in the subject system and method provides the framework for generalized characterization over a range of operating conditions and sprinklers (nozzle) geometries. In this compact representation, only a few physically coherent parameters are required, with empirical data potentially enabling approximation of spray details even when comprehensive measurements are not available.

Since sprinkler sprays demonstrate highly stochastic behavior, the spray may be generated by specifying a number of individual drops determined from stochastic distributions based on experimental measurements of these quantities. In FIG. 13A, each initial drop is given four properties on a unit sphere, which include azimuthal angle $\psi$, elevation angle $\theta$, dimensionless drop size d, and a dimensionless drop velocity, u. The droplets are generated on the surface of a sphere originating from the center of the deflector with radius equal to the initiation distance (typically about 0.35 m to complete spray formation). Analysis of the measurements reveals that drops move radially outward from this origin (i.e. velocity angle determined from position angle) so that only the velocity magnitude requires independent consideration. The spray may be completely described in terms of the volume probability density based on solid angle:

$$\int_\theta \int_\psi \int_u \int_d f_V(\theta, \psi, u, d) d\theta \cdot d\psi \cdot du \cdot dd = 1, \quad \text{(Eq. 3)}$$

where the integral represents the complete collection of unique drops accounting for the entire spray volume. The azimuthal angle, $\psi$, for a drop is determined by randomly choosing an outcome space ranging between 0 and 1, and selecting the corresponding ψ according to the cumulative distribution function:

$$F_V(\psi') = \int_0^{\psi'} f_V(\psi) d\psi, \quad \text{(Eq. 4)}$$

where $f_V(\psi)$ represents the volume probability density in ψ integrated over all elevation angles, drops and velocities described by:

$$f_V(\psi) = \int_\theta \int_u \int_d f_V(\theta, \psi, u, d) d\theta \cdot du \cdot dd. \quad \text{(Eq. 5)}$$

Similarly θ is specified through random selection from the outcome space (ranging between 0 and 1) of the conditional probability cumulative distribution function $$F_V(\theta|\psi') = \int_0^\theta f_V(\theta|\psi') d\theta, \quad \text{(Eq. 6)}$$

where $f_V(\theta|\psi')$ represents the conditional volume probability density in θ at a specific azimuthal station ψ' given by:

$$f_V(\theta|\psi') = \frac{\int_u \int_d f_V(\theta, \psi', u, d) du \cdot dd}{\int_\theta \int_u \int_d f_V(\theta, \psi', u, d) d\theta \cdot du \cdot dd}. \quad \text{(Eq. 7)}$$

The local drop size distribution is given by the Cumulative Volume Fraction (CVF), which is:

$$F_V(d|\theta', \psi') = CVF(d) = \int_0^d f_V(\dot{d}|\theta', \psi') d\dot{d}. \quad \text{(Eq. 8)}$$

The local drop velocity is given by:

$$F_V(u|\theta', \psi', d') = \int_0^u f_V(\dot{u}|\theta', \psi', d') d\dot{u}. \quad \text{(Eq. 9)}$$

Using the methods described in previous paragraphs, these cumulative functions are employed to determine the size and velocity of a random drop after the location has been assigned.

Although unwieldy, the four dimensional probability density, $f_V(\theta,\psi,u,d)$, is available from the nearly one million drop size realizations at each test condition. However, more tractable compressed forms of the important conditional probabilities required for spray generation (i.e. Eqs. 4, 6, 8, and 9) have been formulated to gain insight into the spray characteristics and to facilitate CFD (Computational Fluid Dynamics) integration.

The spray characteristics vary azimuthally because of the periodic tine and space geometry of the sprinkler deflector. These distinct spray characteristics are measured separately. Fourier series is used in block 170 (depicted in FIG. 10) to create a continuous interpolating function between adjacent space and tine measurements. For example, the continuous interpolated cumulative distribution function for assigning azimuthal location (and corresponding number density) can be generated from:

$$F_V(\psi) = A(\psi) F_V(\psi_{Tine}) + (1 - A(\psi)) F_V(\psi_{space}) \quad \text{(Eq. 10)}$$

and $$A(\psi) = \frac{a_0}{2} + \sum_{n=1}^{\infty} a_n \cos \frac{n\pi}{T/2} \psi, \quad \text{(Eq. 11)}$$

where T is the angle sum of one tine and one space, $a_0$ and $a_n$ are Fourier coefficients for a square wave determined from the deflector geometry by integrating over the first tine (ψ=0°) defined in block 168 as:

$$a_n = \frac{2}{T} \int_{-T_{tine}/2}^{T_{tine}/2} \cos \frac{n\pi}{T/2} \psi d\psi. \quad \text{(Eq. 12)}$$

Typically, three coefficients calculated in block 168 of FIG. 10 provide a sufficient azimuthal approximation of the measured data. For determining the elevation angle locations, $f_V(\theta|\psi')$ the volume probability density in θ at an azimuthal station ψ' is first curve-fit with a Gaussian distribution to capture the typical local peak in the elevation flux profile created by the tine stream.

After subtracting this characteristic from the measured data, Legendre polynomial functions are used to curve-fit the remainder. The continuous interpolated cumulative distribution function for locating the elevation angle of random drops (and corresponding density) is given by:

$$f_V(\theta|\psi') = \frac{f_0}{\sqrt{2\pi} \sigma} \exp\left(\frac{(\theta - \theta_0)^2}{2\sigma^2}\right) + \sum_{n=0}^{\infty} C_n(\theta) P_n(\cos(\theta)), \quad \text{(Eq. 13)}$$

where $f_0$ is the magnitude of the local volume flux peak, $\theta_0$ is the elevation angle location of the peak (i.e. a characteristic initial trajectory angle), σ characterizes the width of the local peak, $P_n$ are the Legendre polynomials, and $C_n$ are the Legendre polynomial coefficients determined from the experimental data.

Continuous (basis) functions for local drop size distribution are created by first generating continuous functions describing the local characteristic drop size, $d_{v50}$, and distribution width parameter, γ, using Legendre polynomials defined as:

$$f(d_{v50}|\theta', \psi') = \sum_{n=0}^{\infty} C_n(d_{v50}) P_n(\cos(\theta')) \quad \text{(Eq. 14)}$$

and $$f(\gamma|\theta', \psi') = \sum_{n=0}^{\infty} C_n(\gamma) P_n(\cos(\theta')), \quad \text{(Eq. 15)}$$

Local drop size distributions are generated from these parameters using a combined Log-Normal Rosin-Rammler function:

$$CVF(d) = \qquad (Eq.\ 16)$$

$$\begin{cases} \frac{1}{\sqrt{2\pi}} \int_0^d \frac{\gamma/1.15}{\dot{d}} \exp\left(-\frac{(\ln(\dot{d}/d_{v50}))^2}{2(1.15/\gamma)^2}\right) d\dot{d} & (d < d_{v50}) \\ 1 - \exp(-0.693(d/d_{v50})^\gamma) & (d > d_{v50}) \end{cases}$$

first suggested by FM Global [H. Z. Yu, "Investigation of Spray Patterns of Selected Sprinklers with the FMRC Drop Size Measuring System," First International Symposium on Fire Safety Science, New York, pp. 1165-1176].

Local velocity characteristics can also be described with the continuous function generated in block 170. No provision has been included in the current modeling approach to generate local velocity distributions or to generate a local drop size/velocity correlation. This correlation will undoubtedly occur during dispersion due to drag effects. However, it is not clear that a strong drop size/velocity correlation should appear in the near-field (i.e. at spray initiation).

TABLE 1

Spray initiation parameters.

| Flux/ Location | Azimuthal Direction, ψ Fourier Series $\alpha_o, \alpha_n$ - Deflector Geometry | Gaussian | | | Elevation Direction, θ Legendre Polynomials Avg | Shape |
|---|---|---|---|---|---|---|
| d | $d_{v50}$ | Tine | $f_0$ | $\theta_0$ | σ | $C_0$ | $C_n/C_0$ |
|   |   | Space | $f_0$ | $\theta_0$ | σ | $C_0$ | $C_n/C_0$ |
|   |   | Tine |   |   |   | $C_0$ | $C_n/C_0$ |
|   | γ | Space |   |   |   | $C_0$ | $C_n/C_0$ |
|   |   | Tine |   |   |   | $C_0$ | $C_n/C_0$ |
|   |   | Space |   |   |   | $C_0$ | $C_n/C_0$ |
|   |   | Tine |   |   |   | $C_0$ | $C_n/C_0$ |
| v |   | Space |   |   |   | $C_0$ | $C_n/C_0$ |

Table 1 summarizes the compression methodology introduced in the previous paragraphs where the measured volume flux distributions, drop size distributions, and velocity distributions (all azimuthally aligned with the space and tine deflector features) are used to generate analytical functions describing the spatial variation of the drop density, size, and velocity with elevation angle. These Legendre polynomials and Gaussian basis compact functions are defined through a series of coefficients determined from the detailed measurements. These coefficients provide average values and profile shapes for their respective spray characteristics.

Table 1 also illustrates the treatment of the azimuthal variation of the spray characteristics using Fourier series with coefficients determined from the nozzle geometry. Transforming the complex stochastic spray into this compact physically accessible framework provides insight into the essential spray features and aids in quantitative comparisons between sprinklers.

A drop size scatter plot over all elevation angles at an azimuthal location aligned with the tine (ψ=0°) was formed to compare (in block 190 depicted in FIG. 10) the measured spray data (block 166 depicted in FIG. 10) and spray data generated from the compressed spray description (block 172 depicted in FIG. 10).

The analytical expressions formulated in blocks 168, 170, and 172 are capable of generating a spray with details close to the measurements. This excellent agreement was obtained with n=10 for flux and drop size. However, n as low as 5 also demonstrates a sufficient agreement. The analytical expressions generated in block 170 based on coefficients calculated in block 168 (as depicted in FIG. 10) also help to quantify the spray characteristics through their parameters.

For example, at the tine location of ψ=0°, the spray parameters, $\theta_0$=110°, and σ=15° and $q_0^* = q_0''/q_{avg}''$=8 describe the spray angle (i.e. peak location), peak width, and peak flux normalized by the average flux at the initiation radius.

Generating in block 172 the spray with the compact analytical expressions calculated in blocks 168, 170, provides a unique insight into the structure of the spray.

The basis functions derived from the tine and slot measurements and the drop location prediction approach are used to generate the spray shown in FIG.

Figure 13B:
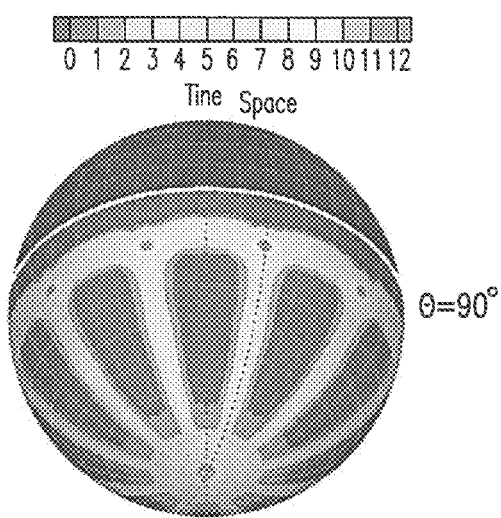
FIG. 13B is a diagram of basis functions distribution of normalized flux based on the spray measurements from the same commercial sprinkler as in FIG. 13A.

The basis functions derived from the tine and slot measurements and the drop location prediction approach are used to generate the spray shown in FIG. 13B, which shows basis function distribution of normalized flux for a commercial sprinkler at injection pressure of 1.4 bar measured at 0.3 m from the sprinkler. The sprinkler is positioned in the center of the unit sphere. The strong variations in flux about the sphere owing to the tine and space geometry are evident. The space stream produces a relatively uniform flux with elevation angle, while the tine stream produces a relatively uniform flux azimuthally.

To evaluate the compression scheme further, flux measurements close to and below the deflector were compared with dispersion predictions initiated with the compressed spray description. The analytical spray is generated in a quiescent air environment and tracked from the initiation location using a Lagrangian particle tracking approach.

However, not every drop in the spray is tracked in this approach. Instead, each drop has a coefficient representing a collection of drops with similar properties (i.e. location, drop size, velocity). The coefficient is adjusted to conserve the volumetric flow rate.

In each time step Δt, for a group of N drops generated and introduced into the spray at the initiation location, the coefficient of each drop is given by:

$$C_N = \frac{Q \cdot \Delta t}{N \cdot \rho \frac{\pi}{6} d_N^3}. \qquad (Eq.\ 17)$$

Drag equations were included to provide one way coupling between the quiescent air and the spray, described by:

$$\frac{d\vec{u_d}}{dt} = \vec{g} - \frac{3}{4}\frac{\rho_g}{\rho_d}\frac{C_d}{d}(\vec{u_d} - \vec{u_g})|\vec{u_d} - \vec{u_g}|. \qquad (Eq.\ 18)$$

where $C_d$ is the drag coefficient, $\rho_g$ is gas density, $\rho_d$ is drop density, $u_g$ is gas velocity, $u_d$ is drop velocity. The simplifying assumption of one way coupling is expected to be valid in this momentum dominated region of the spray.

To further simplify the spray description, only the zeroth order Legendre polynomial is used to describe the velocity (i.e. average spray velocity). Although higher order descriptions of the spray would capture spatial variations in velocity, the simplifying assumption of a single characteristic velocity at initiation was used.

Comparisons were performed in block 190 depicted in FIG. 10 between the predicted (blocks 170-172) and measured (block 166) flux distribution. The linear density of volumetric flux was observed which evidenced an excellent agreement between the predicted and measured fluxes below the nozzle revealing not only the accuracy of the compression approach, but also the suitability of the simplified air-drop coupling for particle tracking near the nozzle exit.

The detailed initial spray measurements performed in the subject methodology reveal the strong relationship between the sprinkler geometry and the resulting spray pattern. The measured volume flux and drop size distributions demonstrate strong directional dependence with azimuthal ($\psi$) and elevation ($\theta$) angles. Correct specification of these quantities is essential for accurate prediction of spray dispersion and volume density distribution at the floor.

The unique framework established in the present system is devised to compress the extensive initial spray data using compact analytical functions capable of high-fidelity spray generation for CFD integration. The compact formulation of the initial spray is capable of generating sprays, which closely resembles the measurements.

Furthermore, dispersion predictions initiated with the analytical functions agree well with volume density measurements obtained below the sprinklers providing additional validation of both the compact initial spray formulation and detailed spray measurements.

The compact analytical functions reveal strong similarities between initial spray characteristics for different sprinkler geometries. Establishing a sprinkler database within this framework provides further insight to quantify typical features of these sprays and thus help to remove the widespread uncertainty associated with specifying the initial sprinkler spray in CFD analysis.

The sprinkler spray foil is distinct sheets based on its tine and slot geometry, as shown in FIG. 11.

FIGS. 12A and 12B show a dispersion, a surface wetting prediction based on preliminary initial spray measurements of a commercial sprinkler (FIG. 12A), and the basis function initial spray data reduction framework (FIG. 12B). The complexity and three dimensionality of the spray are apparent.

The SSSS of the present system provides a comprehensive dataset for determining the basis functions, which would account for details of the sprinkler geometry (i.e. frame arms), which are currently neglected due to insufficient data.

The unique qualities of sprays are exploited for a wide range of applications including propulsion, fire suppression, microelectronic fabrication, pharmaceutical delivery, and others. Designing nozzles/atomizers to generate the spray is often a ‘cut and try’ approach because of the lack of accurate physical models capable of describing the relationship between injection conditions (including geometry) and the resulting spray. Atomization modeling represents a performance limiting ‘missing link’ for computational analysis of a variety of technologies. The high fidelity SSSS measurements provide insight, support atomization model development, and facilitate dispersed phase (spray) CFD simulations. The value of direct visualization of spray details should not be underestimated. Highly resolved (spatially and temporally) quantitative visualization of sprays may lead to new ideas for spray generation technology and engineering practices, in addition to advancing computer based analytical tools.

The measurement approaches underlying the principles of the subject system and method are envisioned in studying the performance of water mist systems from detailed measurements of spray characteristics to exploring the effects of additives on fire suppression performance based on better understanding the role of spray characteristics in fire suppression and establishing models and engineering practices for computational analysis of fire suppression performance.

The SSSS would be used to characterize the nozzles used in the fire suppression studies providing the fidelity necessary to perform simulations of the experiments for model validation and further insight.

In further fire suppression studies, the SSSS is envisioned to facilitate studies on fire/spray interactions, where spray interactions with fire transport processes can be explored including the plume, the flame sheet, and thermal radiation through modeling, canonical experiments, and actual fire tests. It is envisioned that the SSSS would provide initial spray measurements for coarse (sprinklers) and fine sprays (mist) used in actual fire suppression experiments.

In the past, it has been difficult to study fire/spray interactions in a computational framework because the detailed spray characteristics were not available making it impossible to evaluate transport models, CFD transport predictions, and associated fire suppression performance through comparisons with experiment. It is the detailed knowledge of the initial spray delivered by the SSSS, which enables computational modeling and analysis of spray dispersion and spray interaction with the flame.

It is also envisioned to apply SSSS based spray characterization approaches to fire suppression problems address knowledge gaps in fire sprinkler based protection. Specifically, the wetting performance of sprinklers in large high-challenge rack storage configurations can be evaluated where NFPA codes and standards have yet to be developed. Currently sprinkler system design is based upon case-by-case qualification determined from extremely expensive tests without analysis or understanding of safety margins. The empirical approach is inefficient and unsustainable.

The SSSS represents an enabling technology. The initial spray measured by the SSSS along with reduced order computational models can be used in wetting simulations to evaluate and understand the relative fire suppression performance of various sprinkler system designs. The screening analysis is hoped to reduce the number of full-scale fire suppression performance tests required and to improve understanding of the important factors governing the fire suppression system performance.

The SSSS is also envisioned in studying of the behavior of fine sprays used in microelectronics. The small drop size range of the diffraction probe and fast capture rate of the shadowgraphy probe are well suited for characterizing sprays used in this application, for example, in spray technology to produce metal microparticle powders. These powders, formed from inexpensive metal salt precursors, are the dominant ingredient in conductive pastes, which are used in a wide range of applications from hybrid microelectronics to medical devices and photovoltaic modules for solar energy conversion.

An additional area of the SSSS application may include spray pyrolysis which offers many advantages over solution phase routes for powder production. The advantages of spray pyrolysis include: minimal formation of hard aggregates, control of particle size and size distribution through precursor droplet properties, and solvent-free and impurity free final product.

A typical spray pyrolysis system consists of a droplet generator, furnace reactor and particle collection system involving some combination of filtration and inertial separation. Spray pyrolysis has been demonstrated for oxidation resistant metals such as silver and palladium, but extension to base metals (e.g. copper and nickel) has proved challenging.

Hydrogen can be added as a process gas, but concentrations above the flammability limit are typically required in order to produce the desired metallic powders, presenting a safety hazard.

This issue can be addressed by using a co-solvent, ethylene glycol, in addition to water, as a solvent in the initial precursor solution. During spray pyrolysis, the co-solvent decomposes to create a reducing environment in the furnace, and under optimal conditions, dense oxide-free metal powders are produced.

Addition of ethylene glycol, which is much more viscous than water, led to unexpected behavior of the ultrasonic generator. This behavior is of great interest and warrants further exploration to gain insight into the physics of droplet generation and to establish parameter settings for atomization in these applications. Images were acquired using the SSSS, with droplet size distributions measured for two different co-solvent concentrations using an older diffraction based system shown. For the case of water, a fine mist is produced via capillary wave breakup at the top of the cone created by the piezoelectric. With increasing amounts of ethylene glycol (EG), the mist decreases, and a different formation mode is visible, with droplets forming from much bigger waves perpendicular to the surface of the cone. These droplets, will produce metal powders that are too big for conductive paste applications. The overall production rate of the droplet generator, volume of precursor atomized per time, plummets with increased viscosity, thus reducing the overall production rate of the spray pyrolysis system. A detailed analysis of the effects of fluid properties (viscosity, surface tension, density, etc.) is underway. This project would greatly benefit from the SSSS updated diffraction probe targeting the 0.1 to 100 μm range. In particular, the addition of the fast shadowgraphy probe would allow direct imaging of time resolved dynamics of the droplet formation for the case of the large (>50 micron) mode droplets.

The SSSS would provide new capabilities missing in previous measurements, while inspiring collaborators with innovative ways to acquire and evaluate spray characteristics.

The SSSS addresses major challenges associated with spray measurements such as:

(a) obtaining spatially resolved measurements;

(b) obtaining sufficient statistics of essential spray quantities (drop size, velocity, and number); and (c) describing the spray (millions of drop realizations) in terms of a practical number of physically explicit, yet precise, characteristics.

More sophisticated control and automation hardware are envisioned along with much faster lasers and camera equipment to implement the scanning technique for drop measurement. The high-speed laser, camera and computer hardware used in the SSSS make the scanning approach feasible while the increased camera resolution increases the field of view reducing the traversing requirement. The proposed hardware could complete the scan in a very feasible time of about 30 minutes.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of the elements may be reversed or interposed, all without departing from the spirit or scope of the invention as defined in the appended claims.

What is being claimed is:

1. A system for characterization of sprays, comprising:

a nozzle producing a spray under study, and an azimuthal displacement mechanism coupled to said nozzle and configured to actuate a controllable azimuthal displacement of said nozzle about a central axis thereof;

a data acquisition sub-system positioned at a predetermined location with regard to said nozzle and operatively coupled to said spray under study and said azimuthal displacement mechanism and configured to obtain measurement data characterizing a near-field region of said spray under study, wherein said data acquisition sub-system includes:

(a) a laser-based probing sub-system and a translational traverse sub-system operatively coupled to said laser-based probing system-system, said translational traverse sub-system being configured to displace said laser-based probing sub-system to at least one interrogation position with regard to said spray under study for performing substantially complete scanning of an area of interest in said spray under study at said at least one interrogation position, and (b) patternator sub-system disposed at a predetermined position relative to said nozzle of interest in operative connection with said spray under study;

a controller sub-system operatively coupled to said azimuthal displacement mechanism and said translational traverse sub-system and configured to control an azimuthal displacement of said nozzle and actuation and displacement of said translational traverse sub-system with regard to said spray under study in coordination with said azimuthal displacement of said nozzle;

a computer sub-system operatively coupled to said controller sub-system of said data acquisition sub-system, said computer sub-system being configured to track said nozzle displacement and said probing sub-system motion and to instruct said controller sub-system on the controllable azimuthal displacement of said nozzle and controllable motion of said probing sub-system displaced by said translational traverse sub-system with regard to said at least one interrogation position in said area of interest in said spray under study in synchronism with said azimuthal displacement of said nozzle;

a post-processing sub-system operatively coupled to said computer sub-system and configured to process said measurement data acquired by said data acquisition sub-system and generating spray characterization data based on said measurement data;

a data compression processor sub-system operatively coupled to said computer sub-system to receive said spray characterization data therefrom and configured to generate compact basis functions describing said spray under study;

coefficients and parameters calculation sub-system operatively coupled to said post-processing sub-system and configured to calculate coefficients needed for generation of said compact basis functions describing said spray under study;

a spray modeling processor sub-system operatively coupled to said data compression processor sub-system and configured to characterize the spray under study in terms of said compact basis functions; and a product database for said nozzle coupled to said spray modeling processor sub-system and containing compact physical representation of said spray under study.

2. The system of claim 1, wherein said post processing sub-system is configured to process said near-field spray measurement data to generate the near-field spray characteristics therefrom, and wherein said near-field spray characteristics include drops' size and velocity distribution characteristics obtained from said laser-based probing sub-system's measurements and volume flux distribution characteristics of said near-field spray under study obtained from said patternator sub-system's measurements.

3. The system of claim 2, further comprising a memory unit operatively coupled to said data acquisition unit to save said measurement data.

4. The system of claim 2, further including a mapping processor sub-system operatively coupled to said post-processing sub-system, and configured to map said near-field spray characteristics in a spherical coordinate system based on said spray characterization data and tracking data consistent with said azimuthal displacement of said nozzle of interest.

5. The system of claim 2, wherein said coefficients and parameters calculation sub-system is configured to generate average values and profile shapes for said compact functions when said compact basis functions include Legendre polynomials and Gaussian functions, and further to calculate coefficients determined from the nozzle's geometry when said basis compact functions include Fourier series.

6. The system of claim 1, wherein said computer sub-system is configured to instruct said controller sub-system on said controllable azimuthal displacement of said nozzle and controllable motion of said probing sub-system with regard to a plurality of said interrogation positions at said area of interest in said spray under study.

7. The system of claim 1, wherein said probing sub-system includes at least a shadowgraphy probe sub-system, wherein said shadowgraphy probe sub-system is configured to generate images of drops obtained during the scanning of said area of interest in said spray under study, and wherein said computer sub-system processes said images of drops to generate spatial distribution of drops' size, quantity and velocity in said spray under study.

8. The system of claim 1, wherein said probing sub-system includes at least a diffraction probe sub-system configured to measure size of the drops in said spray under study, and wherein said computer sub-system processes said drops' sizes measurements to produce a spatially resolved map of drops' size distribution.

9. The system of claim 1, wherein said probing sub-system includes at least a Particle Image Velocimetry (PIV) probe sub-system configured to obtain images of illuminated said spray under study, and wherein said computer sub-system processes said images to produce spatially resolved characteristic drops' velocities.

10. The system of claim 1, wherein said computer sub-system is configured for coordinating the acquisition of data measurements of said spray under study, scanning of said probing sub-system and said control sub-system operation for tracking of said measurement data sampling.

11. The system of claim 1, wherein said patternator sub-system includes an array of collecting tubes operatively coupled, at one end thereof, to said spray under study to collect water therein, a plurality of containers, each at another end of a respective one of said collecting tubes, and a monitoring unit for monitoring water level change in said containers to measure time rate of said level change, wherein said monitored time rate of level change in said containers is processed by said computer sub-system to obtain volume flux distribution of said spray under study.

12. A method for 3-dimensional (3-D) characterization of a near-field spray produced by a nozzle, comprising the steps of:

(a) forming a Spatially-resolved Spray Scanning System (SSSS), said SSSS including:

a controller sub-system, a nozzle rotating sub-assembly operatively coupled to a nozzle of interest to rotate said nozzle of interest in accordance with commands issued by said controller sub-system, a patternator sub-system disposed at a predetermined distance relative to said nozzle of interest and operatively coupled to a near-field region of a spray produced by said nozzle of interest to assist in measuring flux distribution at a predetermined radius of the near-field spray under study in a plane orthogonal to the nozzle axis, at least one laser-based probe sub-system of a predetermined configuration operatively coupled to said spray under study, and a translational traverse sub-system operatively coupled to said probe sub-system and configured to displace said probe sub-system, under control of said controller sub-system, with regard to said spray for scanning said spray under study to sample at least one interrogation region of interest thereof, said at least one laser-based probe sub-system being configured to obtain drops related measurements;

a laser sub-system operatively coupled to said controller sub-system; and a high speed camera sub-system operatively coupled to said control sub-system;

(b) initiating said spray of interest;

(c) actuating said nozzle rotating sub-assembly for displacing said nozzle of interest azimuthally in accordance to said controller sub-system's commands;

(d) measuring said flux distribution of said near-field spray by said patternator sub-system in coordination with said azimuthal displacement of said nozzle;

(e) displacing, under control of said controller sub-system, said laser-based probe sub-system by said translational traverse sub-system to said at least one interrogation region of interest in said spray under study, and measuring drops related parameters through scanning said near-field spray under study with said at least one laser-based probe sub-system at said at least one interrogation region of interest in synchronism with said azimuthal displacement of said nozzle; and actuating said laser and said camera in accordance with said at least one laser-based probe sub-system's scanning operation; and entering said measured flux distribution and drops related parameters of said near-field spray under study and said azimuthal displacement data in a computer sub-system configured to process said measured characteristics in accordance with a measurement analysis algorithm to create spatially resolved spray characteristics;

(f) applying compact basis functions compression routine to said spatially resolved spray characteristics obtained in said step (e) to generate a compact representation of the spray based on said measured characteristics; and (g) generating a product database for said nozzle of interest containing compact physics based representation of said near-field spray under study computed in said step (f).

13. The method of claim 12, further comprising the step of:

in said step (e), directing said pulsed laser beam onto said spray under study, focusing said high speed camera on said spray under study, synchronizing said pulsed laser and said high speed camera operation to acquire double images of drops in said spray under study separated by a predetermined image separation time interval, applying spatial calibration and image processing to said double images of drops to result in drops' sizes in each said double image, and acquiring drops' velocities through comparison of drops' trajectories obtained from said double images and said image separation time interval.

14. The method of claim 13, further comprising the steps of:

in said step (e), traversing said at least one laser-based probe sub-system with regard to said spray under study, and in said step (c), rotating said nozzle to form a spherical interrogation region covering multiple imaging areas, each azimuthally aligned with predetermined interrogation stations.

15. The method of claim 12, further comprising the step of:

in said step (e), combining individual images of said multiple imaging areas.

16. The method of claim 12, further comprising the steps of:

in said steps (d) and (e), measuring flux distributions, drops' size distributions, and drops' velocity distributions in said spray under study azimuthally correlated with said nozzle rotation, and in said step (f), transforming said spray characteristics into a compact description through the steps of:

generating analytical functions describing spatial variation of said drops' density, size, and velocity in correspondence to an elevation angle, wherein said analytical functions include Legendre polynomials, Gaussian functions, and Fourier series, each defined through respective coefficients determined by processing said measured spray characteristics, wherein said respective coefficients provide average values and profile shapes for said measured spray characteristics, for said Legendre polynomials and Gaussian functions, and wherein said respective coefficients are determined from said nozzle geometry for said Fourier series.

17. The method of claim 12, further comprising the steps of:

in said step (c), measuring azimuthally variable characteristics of said spray under study, and in said step (f), where said sprinkler deflector has a plurality of tines and spaces, applying Fourier series to said measured azimuthally variable characteristics to calculate a continuous interpolation function between said characteristics measured for adjacent spaces and tines.

18. The method of claim 17, further comprising the steps of:

wherein in said step (f), said compact basis functions describe the local characteristic drop size and distribution width parameter, and wherein local drop size distributions are generated from said local characteristic drop size and distribution width parameter by applying a combined Log-Norman-Rosin-Ramnler function.

19. The method of claim 12, further comprising the step of:

in said step (e), applying shadowgraphy imaging to said spray under study containing drops ranging in size from 0.1 mm to 10 mm to measure spatial distribution of drops sizes, number and velocity.

20. The method of claim 12, further comprising the step of:

in said step (e), applying diffraction imaging to said spray under study containing drops ranging in size from 0.1 µm to 100 µm to measure number and size of said drops.

21. The method of claim 12, further comprising the step of:

in said step (e), applying Particle Image Velocimetry (PIV) to measure drops velocities in said spray under study, where said drops range in size from 0.1 µm to 100 µm.

* * * * *